(12) United States Patent
Dae et al.

(10) Patent No.: US 6,866,638 B2
(45) Date of Patent: Mar. 15, 2005

(54) TEMPERATURE SENSING SYSTEM WITH RETROGRADE SENSOR

(75) Inventors: Michael W. Dae, Belmont, CA (US); Timothy R. Machold, Moss Beach, CA (US); Paul M. Stull, San Mateo, CA (US)

(73) Assignee: Radiant Medical, Inc., Redwood City, CA (US)

( * ) Notice: Subject to any disclaimer, the term of this patent is extended or adjusted under 35 U.S.C. 154(b) by 0 days.

(21) Appl. No.: 10/217,188

(22) Filed: Aug. 12, 2002

(65) Prior Publication Data

US 2004/0030259 A1 Feb. 12, 2004

(51) Int. Cl.⁷ .................................................. A61B 5/00
(52) U.S. Cl. ....................................... 600/549; 374/100
(58) Field of Search ................................ 600/474, 549, 600/504, 505; 374/100

(56) References Cited

U.S. PATENT DOCUMENTS

| | | | |
|---|---|---|---|
| 3,369,549 A | 2/1968 | Armao | |
| 3,425,419 A | 2/1969 | Dato | |
| 3,726,269 A * | 4/1973 | Webster, Jr. ................ | 600/526 |
| 4,038,519 A | 7/1977 | Foucras | |
| 4,153,048 A * | 5/1979 | Magrini ...................... | 600/505 |
| 4,298,006 A | 11/1981 | Parks | |
| 5,211,631 A | 5/1993 | Sheaff | |
| 5,269,758 A | 12/1993 | Taheri | |
| 5,403,281 A | 4/1995 | O'Neill et al. | |
| 5,486,208 A | 1/1996 | Ginsburg | |
| 5,531,714 A * | 7/1996 | Dahn et al. ................. | 604/264 |
| 5,531,776 A | 7/1996 | Ward et al. | |
| 5,624,392 A | 4/1997 | Saab | |
| 5,716,386 A | 2/1998 | Ward et al. | |
| 5,733,319 A | 3/1998 | Neilson et al. | |
| 5,776,079 A * | 7/1998 | Cope et al. ................. | 600/585 |
| 5,837,003 A | 11/1998 | Ginsburg | |
| 6,019,783 A | 2/2000 | Philips et al. | |
| 6,096,068 A | 8/2000 | Dobak, III et al. | |
| 6,146,411 A | 11/2000 | Noda et al. | |
| 6,231,594 B1 | 5/2001 | Dae | |
| 6,264,679 B1 | 7/2001 | Keller et al. | |
| 6,290,717 B1 | 9/2001 | Philips | |
| 6,299,599 B1 | 10/2001 | Pham et al. | |
| 6,383,144 B1 * | 5/2002 | Mooney et al. ............. | 600/549 |
| 6,514,214 B2 * | 2/2003 | Kokate et al. .............. | 600/549 |

FOREIGN PATENT DOCUMENTS

WO    WO 00/10494    3/2000

* cited by examiner

Primary Examiner—Eric F. Winakur
Assistant Examiner—Jonathan Foreman
(74) Attorney, Agent, or Firm—Fulwider Patton Lee & Utecht, LLP

(57) ABSTRACT

A temperature sensing system and method for determining a patient's core body temperature by measuring the temperature of the patient's blood at a location in a vessel lumen retrograde of an insertion point of a temperature sensor or sensors into the vessel lumen.

9 Claims, 13 Drawing Sheets

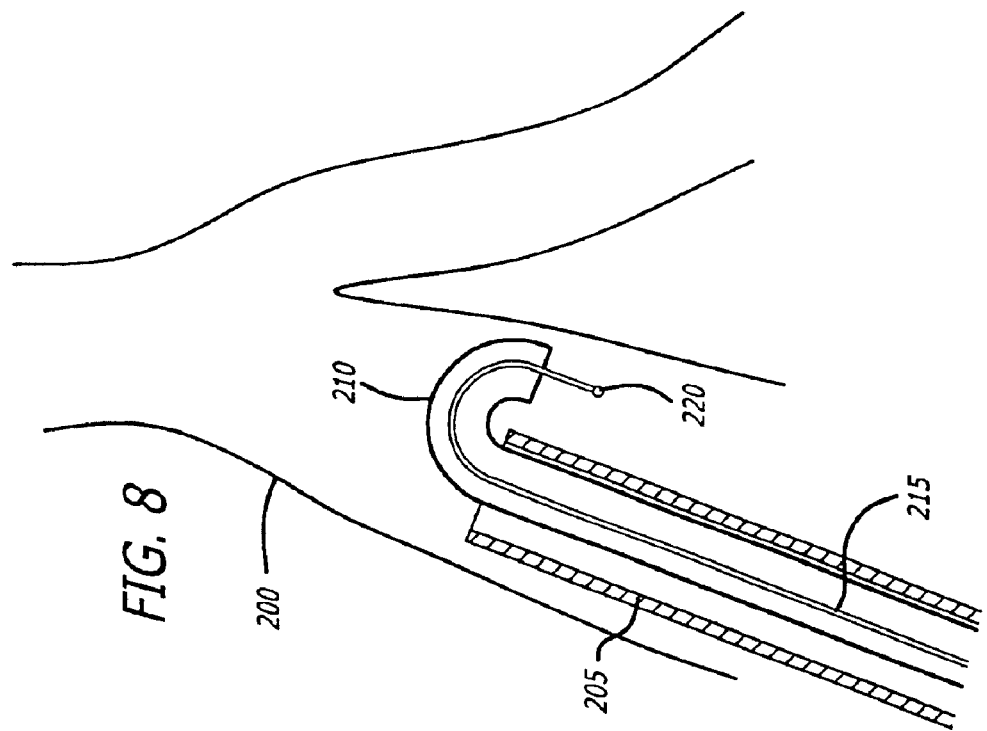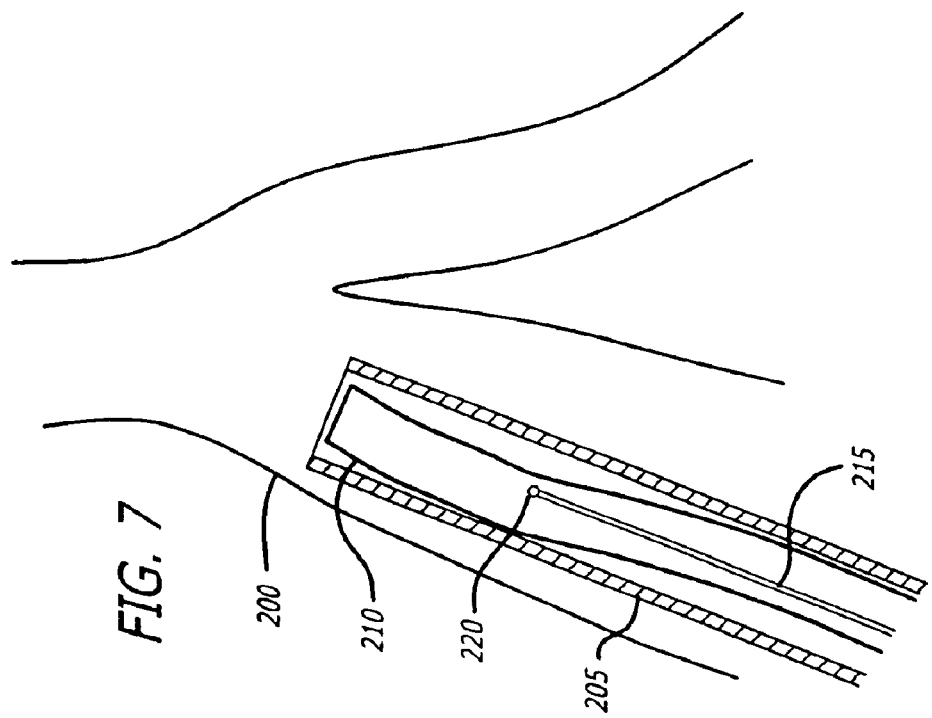

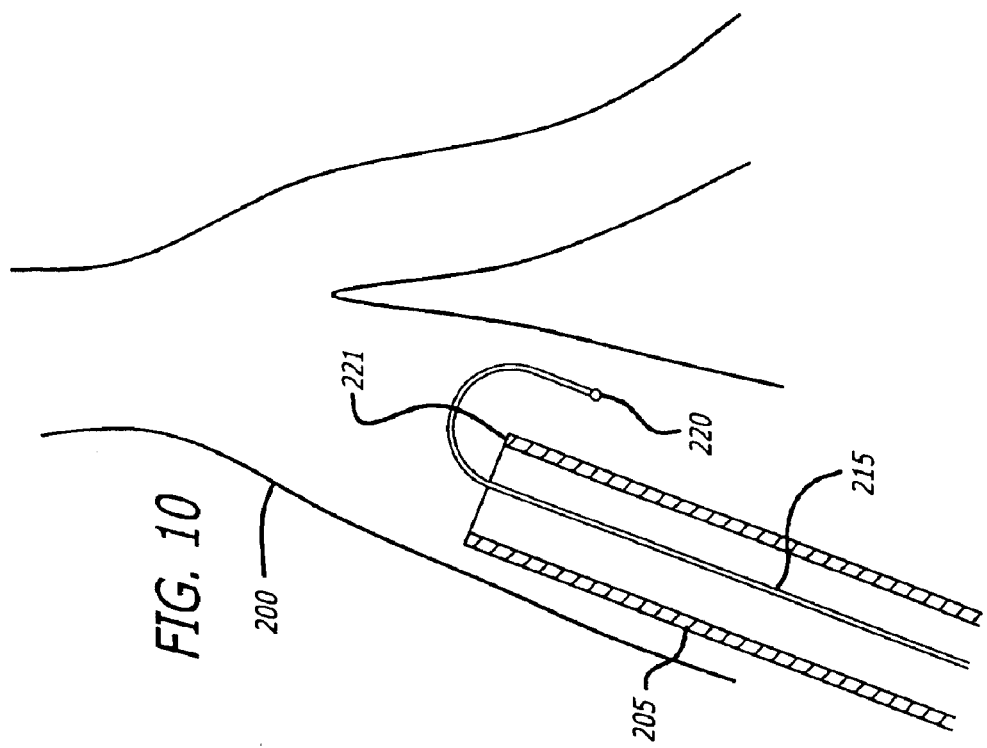
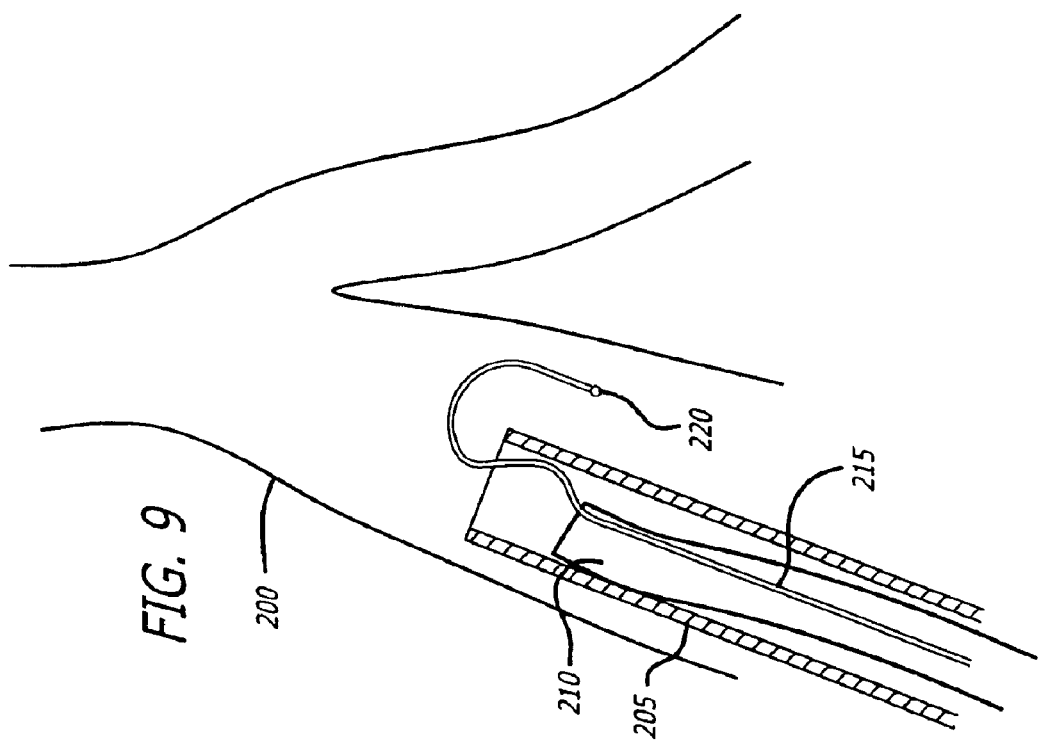

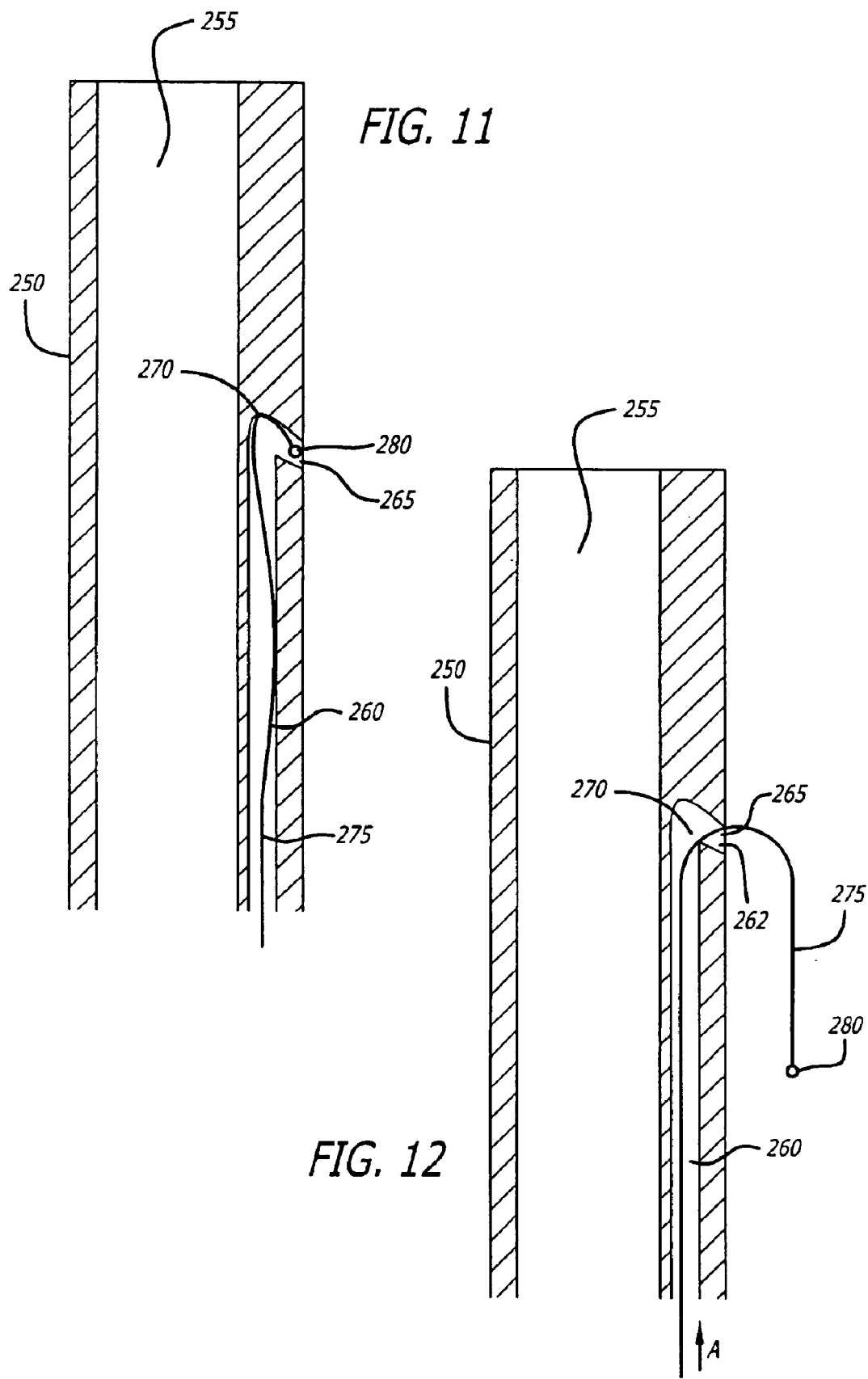

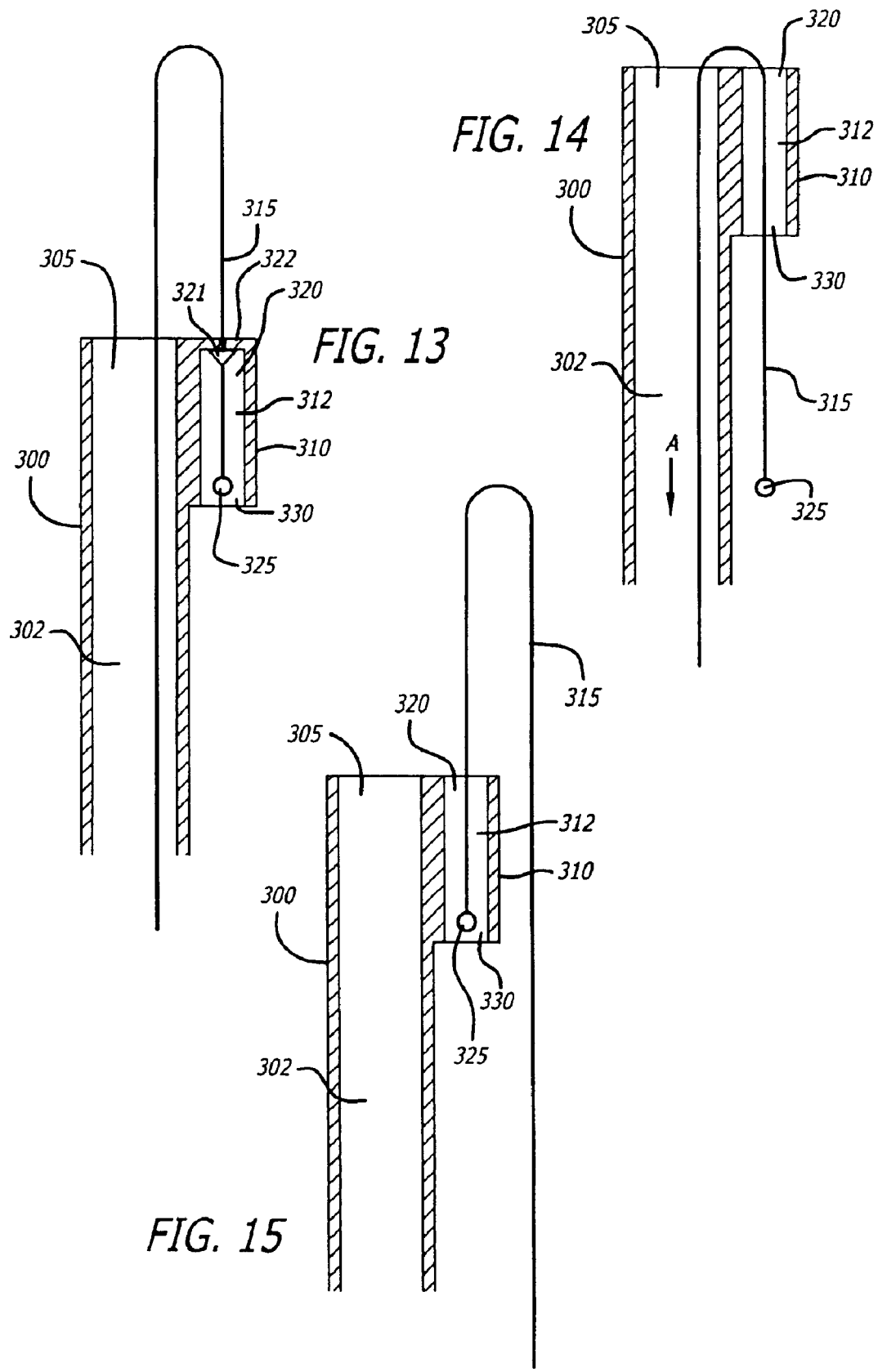

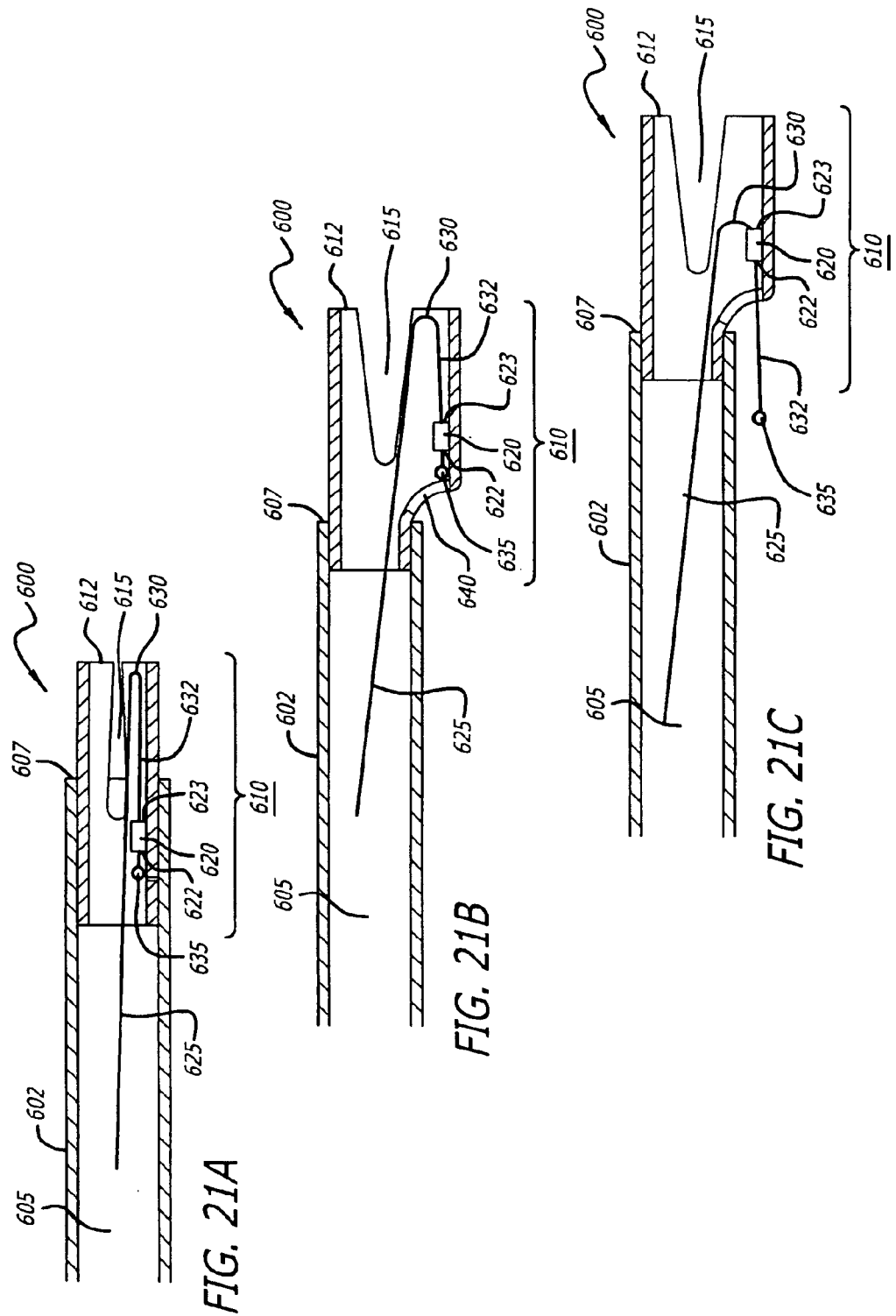

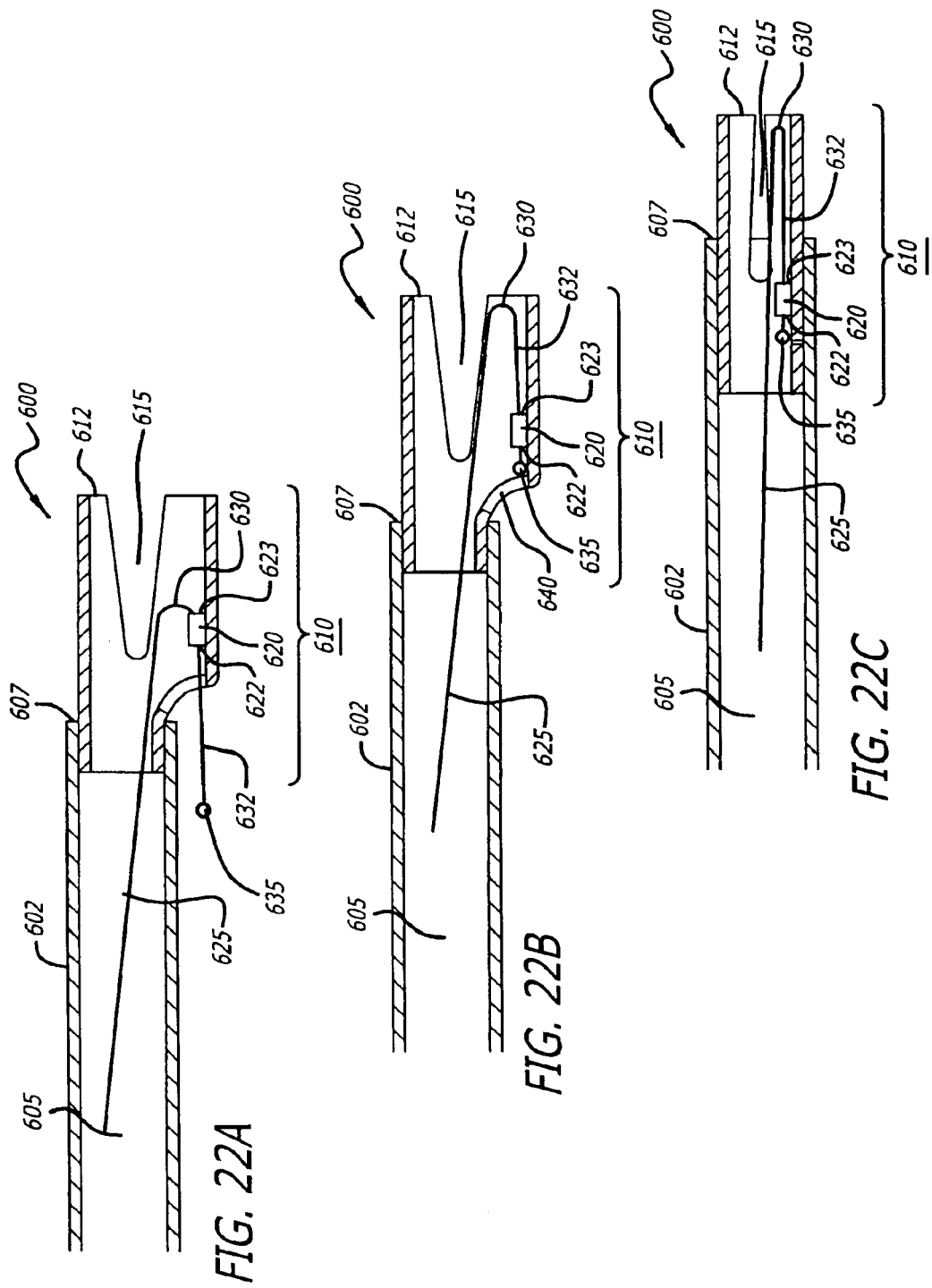

TEMPERATURE SENSING SYSTEM WITH RETROGRADE SENSOR

BACKGROUND OF THE INVENTION

This invention relates generally to a temperature sensing system, and more particularly concerns a device in the form of a probe or modified probe having temperature sensors for deployment through an introducer sheath placed in a body lumen to allow retrograde delivery of the sensors for the measurement or monitoring of the core body temperature.

Under ordinary circumstances, thermoregulatory mechanisms exist in the healthy human body to maintain the body at a constant temperature of about 37° C. (98.6° F.), a condition sometimes referred to as normothermia. To maintain normothermia, the body's thermoregulatory mechanisms act to precisely balance the amount of heat generated by metabolic activity in the body with heat lost to the environment. For various reasons, however, a person may unintentionally develop a body temperature that is below normal, a condition known as hypothermia. In more recent times, hypothermia has been allowed or even induced for various therapeutic purposes.

Accidental hypothermia is generally a dangerous condition that may have serious medical consequences and may result from various conditions such as extreme exposure, injury, illness or anesthesia. Measures are usually taken to restore normothermia to a patient suffering accidental hypothermia. Simple methods for treating hypothermia include wrapping the patient in blankets, administering warm fluids by mouth, and immersing the patient in a warm water bath. If the hypothermia is not too severe, these methods may be helpful. However, if the hypothermia is severe, and especially if the patient is undergoing surgery, such methods may be too slow, impractical and ineffective. One cannot wrap patients undergoing surgery in a warming blanket or immerse them in warm water, or ask severely hypothermic patients that may be unconscious, to swallow enough warm liquid to restore normothermia. Furthermore, where external control over body temperature is desired because the physician desires to induce and maintain hypothermia, these methods are generally not powerful enough to defeat the patient's thermoregulatory responses. For example, if a patient is cooled below the shivering threshold, generally about 35.5° C., the body will shiver and generate metabolic heat that will defeat the attempt to cool the patient to hypothermic levels. Even if the body's thermoregulatory responses are disabled by, for example, disease or anesthesia, surface cooling or warming methods are generally not powerful enough to provide control that can keep a patient at a particular temperature. If the patient begins to get too cold or to warm above the target temperature, the surface cooling and warming methods generally cannot react fast enough and with sufficient precision to maintain the target temperature.

Partly in response to the inadequacies of surface application of heat, methods have been developed for adding or removing heat to a patient's body by internal means. A patient being administered breathing gases, for example a patient under anesthesia, may have the breathing gases warmed. This method may be effective but is limited in the amount of heat that can be administered without injuring the lungs. Similarly, a patient receiving IV fluids may have the fluids warmed. This too may be effective in the case of mild hypothermia, but the temperature of the IV fluid is limited by the temperature that will be destructive to the blood, generally thought to be about 41° C.–49° C., and by the amount of fluid that is acceptable to administer to a patient.

A far more invasive method may be used to add heat to a patient's blood, particularly in the case of heart surgery. Blood is removed from a patient, circulated through a by-pass system, heated or cooled, and then reintroduced into the patient's body. This by-pass method is both fast and effective in adding or removing heat from a patient's blood, but has the disadvantage of involving a very invasive medical procedure which requires the use of complex equipment, a team of highly skilled operators, and is generally only available in a surgical setting, usually where the patient has his or her chest opened by a thorachotomy. It also involves mechanical pumping of blood and channeling the blood through various machines and external lines, all of which are generally very destructive of the blood tissue. Because of this, most surgeons avoid placing a patient on by-pass for greater than 4 hours, and if control of the patient's temperature is desired for longer than that time, this method is unavailable.

One method for adding or removing heat from a patient by adding or removing heat from the patient's blood that does not involve pumping the blood with an external, mechanical pump involves placing a heat exchange catheter in the patient's bloodstream and exchanging heat through the catheter. This endovascular temperature management (ETM) technique was described in U.S. Pat. No. 5,486,208 to Ginsburg, the complete disclosure of which is incorporated herein by reference. One method disclosed for doing so includes inserting a catheter having a heat exchange region comprising a balloon into the vasculature of a patient and circulating warm or cold heat exchange fluid through the balloon while the balloon is in the bloodstream.

In successful ETM, in addition to fast and precise changes in a patient's body temperature, fast and precise control over a patient's thermal condition is very desirable. A general apparatus and method of ETM control based on feedback from temperature probes in or on the patient is disclosed in U.S. Pat. No. 6,149,673 to Ginsburg, the complete disclosure of which is incorporated herein by reference. A similar method is described in PCT publication WO 00/10494 to Radiant Medical Inc., the complete disclosure of which is also incorporated herein by reference. In such methods, a signal representing the temperature of a target tissue, which in whole body ETM may be the core body temperature, is directed to a controller from a temperature probe inserted on or in the patient, and the controller then controls the exchange of heat between the heat exchange catheter and the patient's blood flowing past that catheter. That in turn controls the temperature of the patient. With such a method, precise and rapid control is dependent to a large extent on accurate temperature measurement of the target tissue and thus dependent on an accurate temperature probe located at an appropriate site.

Currently, the patient's temperature may be measured by any one of several generally available temperature probes. These include, for example, skin temperature probes, oral thermometers, tympanic probes that may be placed in the ear canal and perhaps even in physical contact with the ear drum, esophageal probes including nasoesophageal probes, rectal probes, bladder probes, temperature sensors placed on an insertion sheath, and temperature probes that may be inserted by needle directly into the target tissue. These may be highly accurate temperature probes for their purpose. However, when used to provide a temperature signal for ETM, each of these probes suffers from significant shortcomings.

Some probes may not give an accurate temperature of the target tissue. For example, if the target is the core temperature of the patient, a skin temperature is generally not an accurate representation of the core temperature; if cardiac muscle is the target tissue, a bladder probe might not be a sufficiently accurate measure of the temperature of that tissue. This is especially true when used in the context of changing temperature, for example when hypothermia is being rapidly induced by cooling a normothermic patient.

For example, lowering the heart temperature to 32° C. may be very beneficial for a heart attack victim, but lowering the temperature to 28° C. might lead to dangerous arrhythmias. A rectal temperature probe is generally very slow to respond to temperature changes in the body's core temperature, and thus if the target tissue is the heart, and the core temperature is being lowered quickly, a controller receiving its temperature signal from a rectal probe might not receive a temperature measurement that represents the current cardiac temperature and thus might continue cooling even after the cardiac tissue has reached a target temperature and the patient's actual cardiac temperature might dangerously overshoot the target temperature of 32° C. and drop the cardiac temperature below 28° C. In similar manner, probes placed in the bladder also tend to lag core body temperature when that temperature is being changed, i.e., when the patient is being cooled or warmed.

Some probes are awkward and too difficult to use. For example, tympanic probes are difficult to place and tend to fall out of the ear during use. Bladder probes are difficult and awkward to place and generally require a slow but constant flow of uring to function accurately. Rectal probes are inconvenient to use, especially where a sterile surgical field is required. A needle probed placed through a hypodermic syringe into the target tissue may be more accurate and precise but would require injecting the probe directly into the patient and may also require radioscopic or fluoroscopic confirmation of placement, procedures that are not always readily available. Such a procedure would also entail a risk to the patient and the discomfort of a needle stick into the target tissue which might be deep within the body.

Where a temperature probe is controlling an ETM procedure and thus is in or on a patient at the same time as an ETM heat exchange catheter, the probe may be unacceptably influenced by the temperature of the catheter and not accurately reflect the temperature of the target tissue, especially if the probe is located too close to the heat exchange catheter. Temperature probes or sensors placed on the insertion sheath, for example, tend to be unduly influenced by the temperature of the heat exchange catheter placed through the sheath. When the probe is placed in the vasculature at a location some distance away from the catheter so as not to be influenced by the catheter, however, it generally requires a second needle stick or incision, and may utilize a vascular site on the patient that is needed by a physician for some other purpose. For example, if the ETM catheter is located in the left femoral vein, and the probe is placed in the right femoral vein, it would require a separate stick, that is, a puncture of the vessel, for the probe and would make it difficult for an interventionalist to perform angioplasty from either the right or the left femoral artery. A temperature probe might be placed through the same introducer sheath used by an ETM heat exchange catheter to access the central vasculature, but in such a case it would generally be lying alongside the catheter and be influenced by the temperature of the catheter. If the heat exchange catheter had a central working lumen as described in the patents and publication described above, and was located in a central vein, for example the Inferior Vena Cava (IVC), a temperature probe might be passed through the working lumen and distal of the catheter to measure the temperature in the blood. Such a probe would not require a second stick to place it into the bloodstream; however, in this configuration the temperature probe would measure the temperature of the blood soon after it passed over the heat exchange surface and thus might not be an accurate measurement of the temperature of a target tissue or organ or a patient's core. In some cases, If the temperature probe is advanced far enough beyond the catheter tip to obtain an accurate measure, it may need to be positioned in or near the heart which could have serious health repercussions. Such a positioning of the probe would also generally require the use of fluoroscopy or x-ray, procedures which are not always available or desirable.

There is a need therefore, especially in the context of ETM which requires accurate temperature information of a patient's target tissue, for a temperature probe that is not unduly influenced by the temperature of the heat exchange catheter, is located to accurately reflect changes in the patient's temperature, may be conveniently placed, will not require that the patient endure additional punctures or surgical procedures, will not usurp other needed surgical or interventional sites, and can be maintained in place throughout the procedure. The present invention fulfills those needs as well as others.

SUMMARY OF THE INVENTION

Briefly, and in general terms, the present invention is embodied in a temperature sensing system that is configured to position a temperature sensor in a retrograde position, relative to a distal end of a sheath inserted into a lumen of a body vessel, sufficiently retrograde of the distal end of the sheath so that the temperature sensor is isolated from any heating or cooling of the body fluid in the lumen caused by thermal interaction of the sheath, or a catheter or other device inserted through the sheath, with the body fluid. More specifically, various embodiments of the present invention provide for positioning a temperature sensor retrograde of a sheath or introducer in a manner that protects the temperature sensor during insertion into the body lumen and facilitates withdrawal of the temperature sensor when the sensor is removed from the body lumen.

In one embodiment, the invention is a temperature sensing catheter system for measuring the core body temperature of a patient within a body lumen consisting of a sheath having a proximal end with a proximal opening, a distal end region having a distal opening disposed at a distal tip of the distal region, and a lumen therebetween. The catheter system also includes a probe having a proximal region and a distal region having a distal tip, with at least one temperature sensor located at the distal tip region of the probe. The probe also has a bend located at the junction between the proximal and distal regions such that the probe may be bent back on itself with the distal region bent back adjacent the proximal region. When the probe is bent in this manner, the probe may be advanced bend first through an introducer. The probe is advanced into the sheath until the distal end region of the probe is advanced beyond the distal end of the sheath, whereupon the distal end region of the probe separates from the proximal end region of the probe and springs open. The proximal portion of the probe may then be pulled back through the sheath moving the distal end of the probe including the temperature sensor to a position in the body lumen retrograde of the sheath.

In keeping with the invention, when the sheath is inserted into the body lumen, the distal portion of the probe up to the bend is longer than the length of the sheath that is within the body lumen. Thus when the probe springs open and is pulled back within the sheath, the distal portion is pulled retrograde in the vessel.

The probe comprises a temperature probe which carries at least one temperature sensor at its distal end. The at least one temperature sensor may be a thermistor, a thermocouple, or any other temperature sensing device suitable for insertion into a body lumen.

In one embodiment, the distal tip of the probe has at least two temperature sensors attached thereto. These at least two temperature sensors can include thermistors or a combination of a thermistor and a thermocouple. A conductor extends to each temperature sensor located on the distal tip of the probe. Further, the temperature sensors can be protected by a thermally insulated portion of the temperature probe to prevent the conduction of thermal energy to or from the temperature sensor in a manner that adversely affects the accurate measurement of the temperature of the body fluid by the temperature sensor.

In another embodiment, the invention includes a controller unit for providing temperature indications and a coupler for coupling at least one temperature sensor to the controller unit. The coupler is attached to the proximal end of the catheter sheath and is configured to electronically couple at the least one temperature sensor to the controller unit.

In an alternative embodiment, the temperature sensing catheter system of the present invention may include a heat exchange type catheter having a heat exchange region. An insulated section of the temperature probe, positioned between the temperature sensor and the portion of the probe that may be effected by the temperature of the heat exchange catheter, prevents heat conduction along the probe to the sensor from the sheath or the heat exchange catheter.

In another embodiment, the invention further includes a controller unit for accepting a temperature signal from said probe and using said temperature signal to control the heat exchange catheter in such a way to control the exchange of heat between said heat exchange catheter and the bloodstream. If more than one sensor is disposed on or in the probe, the redundancy may be used for safety by, for example, checking temperature signals from each of the sensors against each other for consistency.

In yet another embodiment, the invention comprises a temperature sensing system for determining the temperature of a target tissue of patient by measuring the temperature of body fluid flowing with a body lumen, comprising an introducer sheath having a proximal opening, a distal end region having a distal opening disposed at a distal tip of the distal end region, and a lumen therebetween, the lumen having a diameter at the distal opening and a temperature probe having a proximal region and a distal region having a distal tip having at least one temperature sensor mounted thereon, the temperature probe configured so that when inserted into the introducer sheath and advanced into the body fluid flowing within the body lumen, the temperature probe is located retrograde of the distal end region of the introducer sheath.

In still another embodiment, the invention comprises and apparatus for assisting in locating a temperature probe for measuring the temperature of a body fluid flowing within a body lumen at a position retrograde from a distal opening of a lumen of an introducer embodied in a deployment catheter having a proximal end having a proximal opening and a distal region having a distal opening disposed at a distal tip of the distal region, and a lumen defined by a wall extending between the proximal opening and the distal opening, the distal region being expandable from a compressed state when the distal region is disposed within the lumen of the introducer, and also having an expanded state when the distal region is advanced beyond the distal opening of the introducer, the distal region also having a guide tube disposed on an inner surface of the wall, the distal region having a proximal portion having an opening extending through the wall of the proximal portion of the distal region, the opening providing a pathway between the lumen of the deployment catheter and an exterior of the deployment catheter when the distal region is in the expanded state, a probe having a proximal region, a bend region and a distal region, the distal region of the probe having a distal tip, the distal tip and distal region of the probe extending through the guide tube such that the bend region is disposed distal of the guide tube and the distal region is disposed proximal of the guide tube, and a temperature sensor disposed on the distal tip of the probe. The distal end region of the deployment catheter may includes one or more slots to assist in achieving the compressed state. Alternatively, the distal end region may be formed from a flexible material such that the wall of distal end region folds, allowing the distal end region to achieve the compressed state, and to unfold to achieve the expanded state.

The present invention is also directed to a method of measuring the core body temperature of a patient. The method includes providing a catheter system having a sheath having a proximal end with a proximal opening, a distal end region having a distal opening disposed at a distal tip of the distal region, and a lumen therebetween.

The method further includes providing a probe having a proximal region and a distal region having a distal tip, with at least one temperature sensor located at the distal tip region of the probe. The probe also has a bend located at the junction between the proximal and distal regions such that the probe may be bent back on itself with the distal region bent back adjacent the proximal region. When the probe is bent in this manner, the probe may be advanced bend first through an introducer. The probe is advanced into the sheath until the distal end region of the probe is advanced beyond the distal end of the sheath, whereupon the distal end region of the probe separates from the proximal end region of the probe and they spring apart. The proximal portion of the probe is then be pulled back through the sheath and the distal region including the at least one temperature sensors moves in the vessel retrograde of the sheath.

In still another embodiment of the method of the present invention, the distal tip of the probe includes at least two temperature sensors attached thereto consisting of thermistors, or a combination of a thermistor and a thermocouple. A conductor extends to at least one temperature sensor located on the distal tip of the probe. Further, the temperature sensors can be housed in a thermally conductive, electrically insulative material.

Yet another embodiment of the method of the present invention includes providing a controller unit for providing temperature indications and a coupler for coupling the at least one temperature sensor to the controller unit. The coupler is attached to the proximal end of the catheter sheath and is configured to electronically couple the at least one temperature sensor to the controller unit. In this embodiment, signals representing the temperature sensed by the at least one temperature sensor are communicated to the controller unit through the coupler. If more than one sensor is disposed in or on the probe, the method may include comparing the signals from each of the sensors against one and other to determine the consistency of the measurements. The controller may then command an appropriate response to any inconsistent or out of range temperature signals from one or more of the sensors. Such a response may include, but is not limited to, alerting the operator of the controller that an inconsistency exists, waiting a predetermined period of time and then comparing the signals from the sensors again to determine if the inconsistency was an artifact or a real inconsistency, and/or automatically commanding the controller to maintain the last temperature for which there is data the controller may rely on to determine that the measurement was satisfactory.

In another embodiment, the method of measuring the core body temperature of a patient includes the use of a heat exchange type catheter having a heat exchange region. An insulated section of the temperature probe, positioned between the temperature sensor and the portion of the probe that may be effected by the temperature of the heat exchange catheter, prevents heat conduction along the probe to or from the sensor to or from the sheath or the heat exchange catheter.

Other features and advantages of the present invention will become more apparent from the following detailed description of the invention when taken in conjunction with the accompanying exemplary drawings.

BRIEF DESCRIPTION OF THE DRAWINGS

FIG. 7 is a cross-sectional view of an alternative embodiment of the present invention depicting a "J" introducer tube within a sheath to guide a temperature probe into a retrograde position;

FIG. 8 is a cross-sectional view of the embodiment depicted in FIG. 7 showing the introducer tube in position within the lumen of a vessel;

FIG. 9 is a cross-sectional view of the embodiment of FIG. 7 showing location of a temperature probe and withdrawal of the introducer tube;

FIG. 10 is a further depiction of the embodiment of FIG. 7 showing the temperature probe located within a vessel and the introducer completely withdrawn;

FIG. 11 is an alternative embodiment of the present invention showing a sheath having a central lumen and a side lumen with a temperature wire in the side lumen;

FIG. 12 is a further depiction of the embodiment of FIG. 11 showing a temperature wire advanced through the side lumen of the sheath to locate the temperature probe in a retrograde position;

FIG. 13 depicts an alternative embodiment of the present invention illustrating a sheath having a capture portion located at the distal end of the sheath;

FIG. 14 shows the embodiment of FIG. 13 with a temperature wire extending through the central lumen of the sheath and into a side lumen of the capture portion to locate a temperature probe in a retrograde position;

FIG. 15 is a cross-sectional view of a further embodiment of the invention.

FIGS. 21A–21C are partial cross-sectional views of an alternative embodiment of the present invention including a deployment catheter having a collapsible and expandable distal region, the distal region including a port allowing a temperature sensor to be guided into a retrograde position; and FIGS. 22A–22C are partial cross-sectional views of the embodiment of FIGS. 21A–21C showing the removal of the temperature sensor from the retrograde position.

DETAILED DESCRIPTION OF THE PREFERRED EMBODIMENTS

The present invention provides apparatus and a method for measuring the core body temperature within a body lumen of a patient using a temperature sensing probe. In particular, the temperature sensing probe of the invention includes at least one temperature sensor selectively located retrograde of an introducer sheath inserted within a blood vessel during a medical procedure for measuring the temperature of the fluid flowing through the blood vessel to determine the core body temperature of patient. Such retrograde positioning of the temperature sensor protects the temperature sensor from being affected by any heating or cooling of the blood caused by the sheath or a catheter or other instrument inserted into the vessel through the introducer sheath. In this manner, the temperature sensing system of the present invention provides a system and method for determining and monitoring the core temperature of a patient so that adjustments to the patient's core temperature may be made in a controlled manner using a heat exchange catheter system, or any other system designed to controllably alter the temperature of body fluids flowing through vessel, and thereby, controllably alter the core temperature of the patient.

In the following detailed description, numerous specific details are set forth in order to provide a more thorough understanding of the present invention. However, it will be apparent to those skilled in the art to which this invention pertains that the present invention may be practiced without these specific details. In other instances, well-known devices, methods, procedures, and individual components have not been described in detail so as not to obscure aspects of the present invention.

Figure 1:
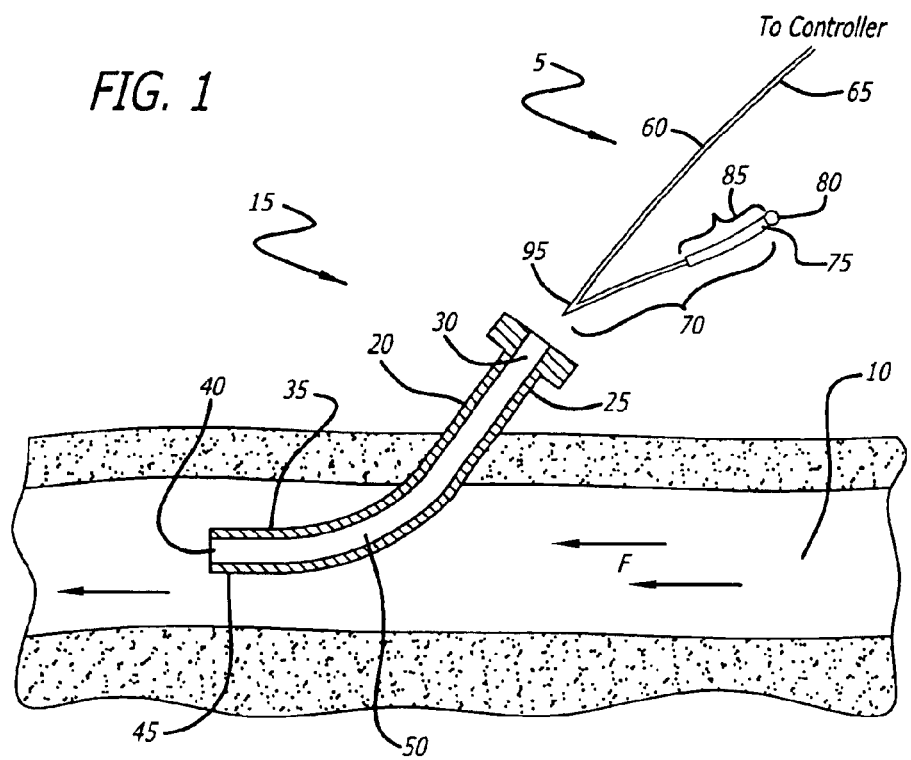
FIG. 1 is schematic of one embodiment of a temperature sensing probe according to the present invention showing an introducer sheath inserted percutaneously into a blood vessel of a patient.

Referring now to the drawings, wherein like reference numerals designate like or corresponding elements among the several views, there is shown in FIG. 1 a temperature sensing system 5 according to the present invention which has been partially inserted through the patient's skin into a blood vessel 10. Blood flow through the vessel is indicated by a set of flow arrows F. Preferably, the catheter is inserted into a relatively large blood vessel, such as the femoral artery or vein, inferior or superior vena cava, or the jugular vein. These blood vessels are particularly advantageous because of accessibility within the patient's body and safe and convenient insertion sites along those vessels, and supply of relatively large volumes of blood flowing therethrough. The femoral artery and vein and the jugular vein are also advantageous locations for heat exchange systems in that they provide access to relatively long, straight blood vessels and thus may provide for easy placement of heat exchange elements into those vessels. For example, the femoral vein is generally 36–42 French (12–14 mm diameter; one millimeter of diameter is 3 French), and thus may accommodate a relatively large diameter catheter without significant obstruction of blood flow. A heat exchange catheter maybe advanced through the femoral vein to place the heat exchange region into the inferior vena cava (IVC) which may be about 25–35 cm long and generally at least 66 French in diameter. Thus a heat exchange region, such as a heat exchange balloon located on the portion of the heat exchange catheter located in the IVC may be very large when expanded (e.g. 25 French) without causing any significant obstruction to blood flow. Similarly, the jugular vein may have a diameter of about 22 French or slightly more than 7 mm. A heat exchange catheter may be advanced through the jugular vein to place into the superior vena cava (SVC) as is commonly done with central venous lines. Although the SVC itself is rather short (only about 6 cm) the length for insertion using this insertion cite is about 15–20 cm, and the diameter of the vessels 14–20 mm (42–60 Fr.). Accordingly, a catheter suitable for insertion into these vessels can be made quite large compared to catheters which are inserted into other, smaller, regions of the vascular system.

With further reference to FIG. 1, there is shown an elongated introducer sheath 20 with a proximal end 25 having a proximal opening 30, a distal end region 35 having a distal opening 40 disposed at a distal tip 45 of the distal end region 35, and an inner lumen 50 which extends within the introducer sheath from the proximal end thereof to the distal opening located in the distal end of the sheath. The distal end region of the sheath is capable of being percutaneously introduced into a biological site, such as a blood vessel 10, of a patient.

In one embodiment of the present invention as shown in FIG. 1, the temperature sensing system 5 is used for measuring the core body temperature of a patient by measuring the temperature of the blood or other body fluid flowing through the body lumen 10. A probe 60 having a proximal region 65, a distal region 70, a bend 95 between the distal and the proximal regions, and a distal tip 75, extends longitudinally through the lumen of the sheath. As is known in the art, the sheath lumen 50 which receives the probe is sized for receiving various diameter guide probes, catheters or other medical devices to suit a particular application.

Associated with the temperature sensing system 5 is at least one temperature sensor 80 for determining the temperature of the blood or body fluid retrograde (in this case upstream) from the inserted portion of the sheath 20 within the blood vessel 10 from which the core temperature of the patient may be accurately determined. In one embodiment, the distal tip 75 of the probe 60 has at least one temperature sensors mounted thereon. In another embodiment, there are two or more temperature sensors mounted on the distal tip 75 of the probe. In yet another embodiment, a plurality of temperature sensors may be mounted along distal region 70 of the probe 60.

The temperature sensor or sensors mounted on the probe 60 may be thermistors, thermocouples or some other device suitably sized and configured to measure the temperature of the blood or body fluid flowing through the lumen of vessel 10. Alternatively, the type of sensor may be mixed, that is, for example, one sensor may be a thermistor and one sensor may be a thermocouple, where there are two or more temperature sensors mounted on probe 60. Each temperature sensor may provide a temperature signal to a controller (not shown) which is indicative of the temperature of the distal tip at that sensor. The temperature signal from the temperature sensor or sensors is transmitted to the controller over a conductor or lead. The conductor or lead may be an insulated wire formed from materials that are biocompatible yet resist degradation by body fluids or blood.

Preferably, the temperature sensing system 5 of the present invention further includes a coupler 521 for coupling at least one temperature sensor 80 to a cable 522 in electrical communication with the controller 535. The coupler is attached to the proximal end 530 of the conductor and is configured to electronically couple the conductors or leads from the temperature sensor or sensors to a cable or other means so as to connect the temperature sensors to the controller unit. In this manner, signals generated by the temperature sensor or sensors are communicated to the controller, where they may be used as input for a microprocessor based controller. The microprocessor based controller monitors the temperature signals and controls the circulation rate and temperature of the fluid flowing through a heat exchange catheter to warm or cool blood flowing through the blood vessel to alter or maintain the temperature of a target tissue, or the core temperature of the patient. For example, when the controller determines from the temperature signals that the temperature of the blood upstream of the heat exchange catheter is too high, the controller causes an increased flow of cooling fluid, or a decrease in the temperature of the cooling fluid, or both simultaneously, to provide additional cooling to the blood flowing past the heat exchange region of the heat exchange catheter. The controller monitors the temperature signals and may continually adjust fluid temperature or flow rate, or both simultaneously, in response to those signals to reach the desired blood temperature. The monitoring and controlling functions of the microprocessor based controller may use various algorithms so that the desired temperature is reached, and maintained, with as little over or undershoot as possible. Similarly, the same system is responsive to temperature signals indicating that the blood temperature is too low so as to increase the temperature of the blood. While a control system utilizing a microprocessor is described, it will be understood that analog systems may also be used to obtain the same temperature control in response to the temperature signals provided by the temperature sensors located at a position retrograde of the heat exchange catheter.

Figure 5:
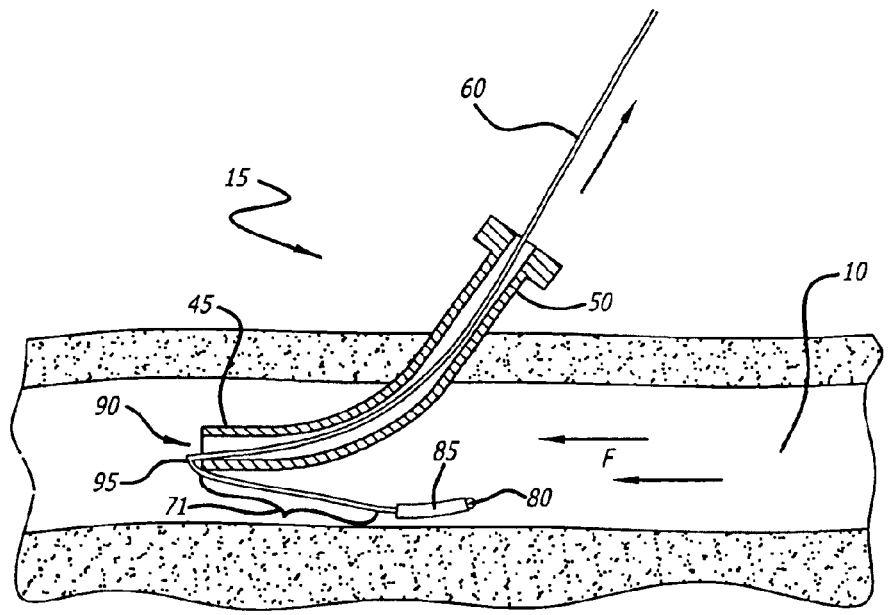
FIG. 5 is a schematic of the temperature sensing catheter system depicting the probe of FIG. 2 within the blood vessel in a retrograde position.

With further reference to FIG. 1, the temperature sensing system 5 of an embodiment of the present invention includes an insulator sleeve 85 which may house the temperature sensors 80 therein or may be located between sensors and the portion of the probe shaft 71 adjacent the introducer sheath when the probe is inserted (see FIG. 5). The insulator sleeve is made of a biocompatible material that is sufficiently resistant to degradation resulting from contact with blood or other body fluid and which is suitably insulative to prevent thermal energy from being conducted along the probe to the temperature sensor. This embodiment is advantageous in that it assists in isolating the temperature sensor to improve accuracy of the measurement of the temperature of the body fluid in which the temperature sensor is immersed. Because the insulator sleeve is thermally insulating, the sensors located within the sleeve may be selectively potted with a thermally conducting material to ensure that the sensors are in thermal contact with the blood or fluid stream in which the sensors are immersed.

Figure 2:
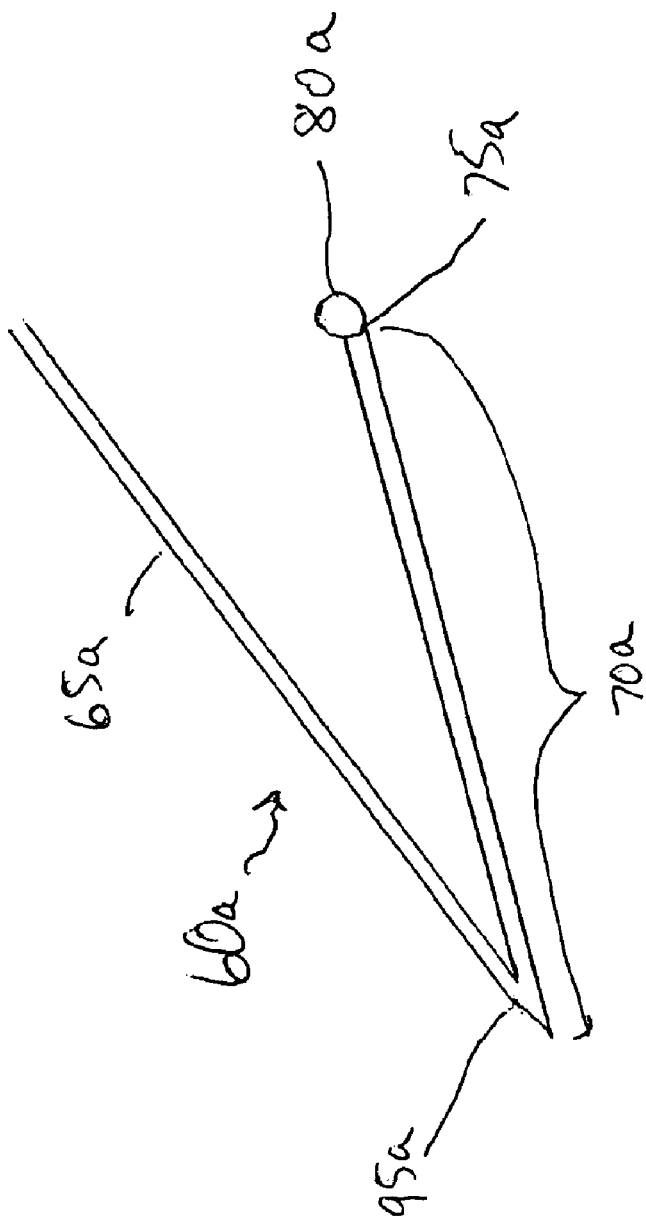
FIG. 2 is a schematic, elevational view of one embodiment of the temperature sensing probe according to the present invention.

FIG. 2 illustrates a schematic, elevational view of one embodiment of the probe 60 in accordance with the present invention. An intermediate portion 90 of the probe 60 has a bend 95 formed therein such that the probe assumes a doubled-over configuration while being inserted into the proximal opening 30 of the sheath 20 (FIG. 3).

Figure 3:
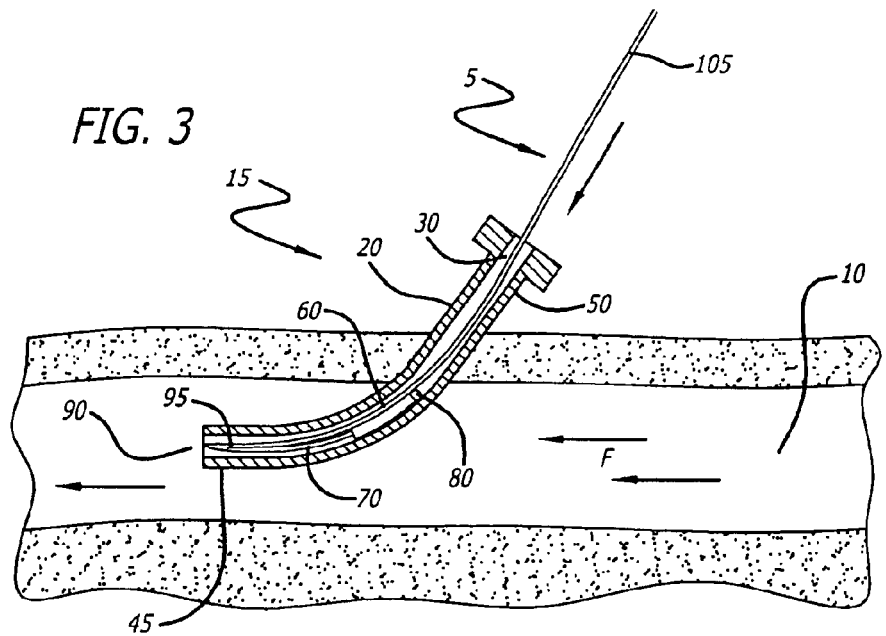
FIG. 3 is a schematic of the temperature sensing probe of FIG. 2 inserted into a sheath of the temperature sensing catheter system while in a doubled-over configuration.

FIG. 3 illustrates the sheath 20 partially inserted into the body lumen 10 of the patient. The probe 60 is first introduced into the proximal opening 30 of the sheath 20 and then advanced through the inner lumen 50 of the sheath. As shown in FIG. 3, the probe has a bend 95 located adjacent to the beginning of the distal end region 70 such that when the probe is inserted in the lumen of the sheath, the probe bends back upon itself and the bend in the probe is the leading portion of the probe as it is advanced through the introducer sheath.

Figure 4:
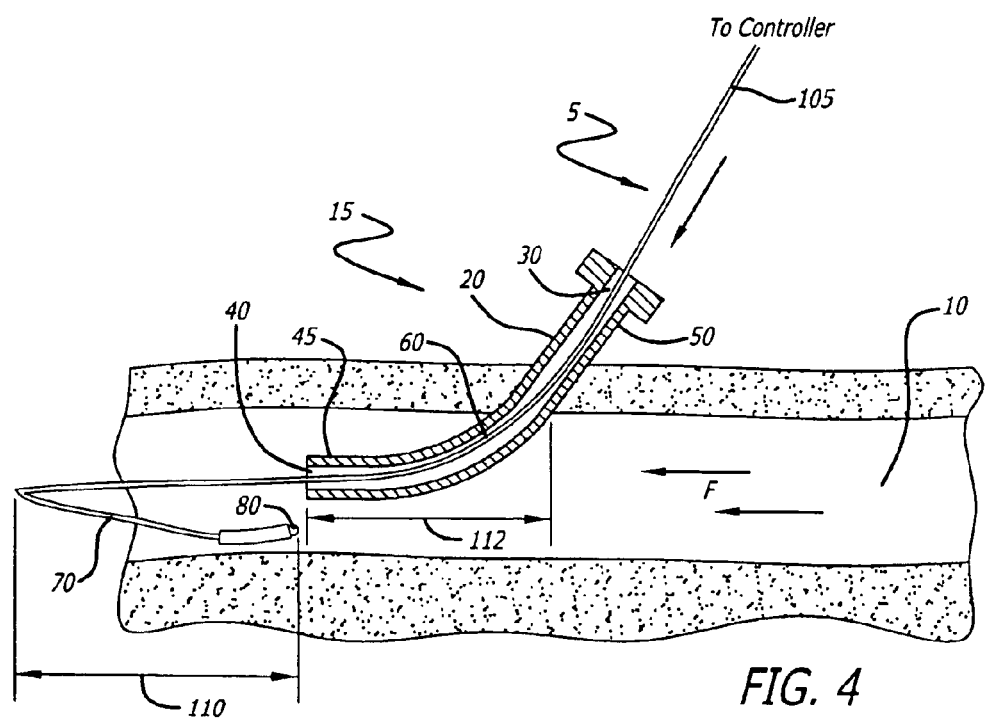
FIG. 4 is a schematic of temperature probe of FIG. 2 showing the distal portion of the probe advanced out the distal end of the sheath.

Typically, as shown in FIG. 4, the distal region 70 of the probe 60 up to the bend 95 has a length 110 that is longer than the length 112 of the portion of the sheath inserted within the body lumen. The length of the probe 60 from proximal end 105 to the bend 95 is generally longer than the length of probe 60 from bend 95 to distal tip of probe 60. It should be appreciated that the length of the probe can vary depending on factors such as the size of the catheter used and the type of medical application employed so as to ensure that the temperature sensor or sensors are positioned far enough retrograde of the sheath to ensure accurate measurement of the temperature of fluid flowing through body lumen 10, free of any influence resulting from proximity to the sheath or any other catheters or instrumentation also inserted into the body lumen through the sheath.

The distal region 35 of the probe 60 separates from the proximal region 65 of the probe and springs open from its doubled-over configuration when the distal tip with temperature sensor 80 exits the distal opening 40 of the distal tip 45 of the sheath. FIG. 5 illustrates placement of the distal end region 75 of the probe and temperature sensor 80 in a retrograde position retrograde of the sheath within the blood vessel.

Figure 6:
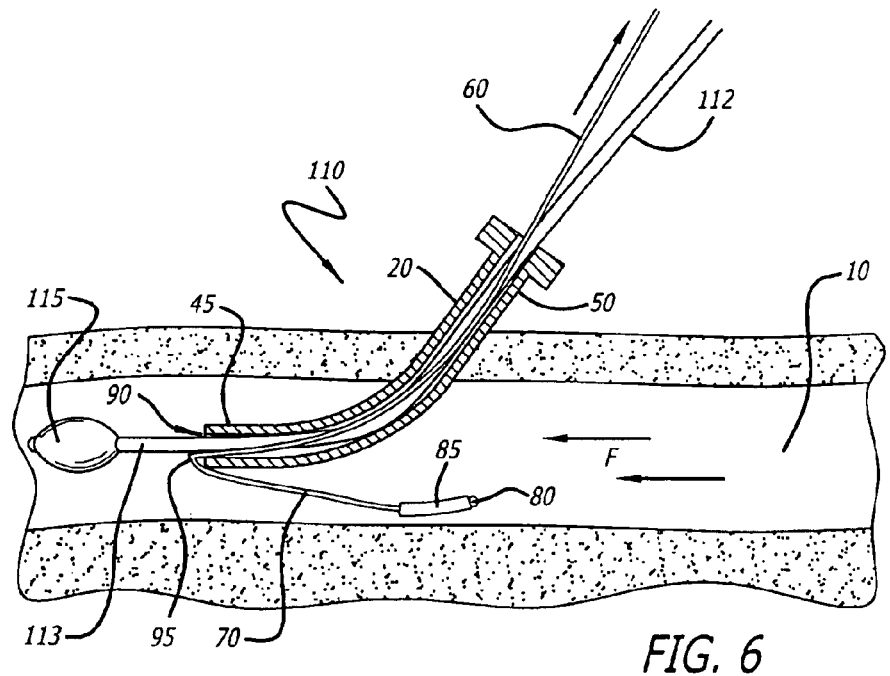
FIG. 6 is a schematic depicting the retrograde position of the probe of FIG. 2 relative to a heat exchange catheter inserted through the sheath into a vessel lumen.

In FIG. 6, a temperature sensing system 110 in accordance with the present invention is depicted along with a heat exchange catheter 112 having a heat exchange region 115 disposed on a distal end of the catheter 112 inserted into the vessel 10 through a catheter sheath 20. The distal end of the catheter 112 is typically advanced through the lumen of sheath 20 and into vessel 10 until the heat exchange region 115 of the catheter 112 is positioned at a desired location within vessel 10.

A typical heat exchange catheter 112 employs a fluid flowing through lumens in the heat exchange catheter to provide thermal energy to or remove thermal energy from the heat exchange region 115 of the catheter attached to the distal portion of a catheter shaft 113. Heat exchange region 115 is typically configured to exchange thermal energy with the blood or body fluid flowing past heat exchange region 115 so as to raise or lower the temperature of the blood or body fluid. An example of a heat exchange catheter may be found in publication WO 01/58397 A1 entitled Multiple Lumen Heat Exchange Catheter, the entire disclosure of which is incorporated herein by reference.

Although heat exchange region 115 is depicted in FIG. 6 as a balloon in which heat exchange fluid is circulated into and out of, heat exchange region 115 may take different forms. The shape, structure and configuration of the heat exchange region is dependent on the needs of the particular procedure or vessel in which the heat exchange catheter is placed, and any configuration may be used so long as the size, profile and function of heat exchange region 115 are such that the heat exchange region 115 may be advanced through the vascular system and positioned where desired without inappropriately interfering with the flow of blood or fluid through the vessel.

It should be appreciated that the fluid flowing though the catheter will affect the temperature of the catheter shaft and the temperature of the sheath. The shaft, the sheath and the heat exchange region will each affect the temperature of the blood as it flows downstream, so that a sensor placed in that portion of the bloodstream will not detect a temperature that accurately and reliably represents the core body temperature of the patient. The temperature sensing system of the present invention, however, enables the positioning of a temperature sensor retrograde of the sheath, heat exchange catheter shaft and heat exchange region 115 to minimize if not eliminate the effect of the thermal energy being transferred by the heat exchange catheter on the temperature sensor. In this manner, the temperature sensor system of the present invention enables accurate determination of blood or body fluid temperature, and subsequent interpolation to determine the core temperature of the patient.

The temperature sensing system of the present invention may further include a control unit (FIG. 19) which generally controls a heating or cooling device adapted to provide warming or cooling fluids to the heat exchange catheter. The controller controls the heater/cooler in response to temperature signals received from the temperature sensor or sensors deployed in the vessel in order to control the temperature of the heat exchange region 115 at a desired temperature to heat, cool or maintain the desired temperature of the target tissue or whole body temperature of a patient.

The present invention also provides a method for determining a patient's core body temperature by measuring the temperature of the patient's blood or body fluid using a temperature sensor or sensors disposed with a body lumen 10 retrograde of an inserted sheath 20. The method consists of providing a sheath 20 of the type described in connection with FIG. 1. The sheath is first positioned with its distal opening 40 within the body lumen 10 of the patient. The method further includes providing a probe 60 having a proximal region 65, a distal region 70, and a distal tip 75, which extends longitudinally through the lumen of the sheath (FIG. 3). At least one temperature sensor 80 is attached to the probe's distal tip.

As shown in FIG. 3, the sheath 20 is inserted percutaneously into the body lumen 10 of the patient. The probe 60 is first introduced into the proximal opening 30 at the proximal end 25 of the sheath 20. The probe 60 has a bend 95 located adjacent to the beginning of the distal end region 70 such that when the probe is advanced through the lumen 50 of the sheath, the probe bends back upon itself so that the distal region 70 of the probe is adjacent the proximal region of the probe forming a doubled-over configuration. The probe 60 is then advanced longitudinally through the lumen 50 of the sheath 20 until the temperature sensor or sensors 80 are advanced beyond the distal opening 40 at the distal end 55 of the sheath, at which point the distal end region of the probe 70 separates from the proximal end region of the probe and springs open, as shown in FIG. 4.

With further reference to FIG. 4, the distal region 70 of the probe 60 up to the bend 95 is of a length that is longer than the length of the portion of the sheath 20 that is inserted within the body lumen 10. Following the passage of the distal region of the probe from the distal opening 40 at the distal tip 45 of the sheath 20 and into the vessel 10, the distal region of the probe is navigated in a retrograde direction along the sheath to position the sensor or sensors retrograde of the sheath within the body lumen (FIG. 5). The temperature of the flowing body fluid, e.g. blood, is then measured by the retrograde sensor or sensors to generate a temperature signal representative of the temperature of the target tissue, e.g. the core body temperature or the temperature of the cardiac tissue.

This temperature signal may then be transmitted to a controller 535 (FIG. 19), which, in response to said temperature signal controls a heat exchanger such as a heat exchange balloon 507 located on a heat exchange catheter 505 in the patient's vasculature, such as in the femoral artery 510. This in turn may control the temperature of the target tissue, for example the core body temperature of a patient.

Referring now to FIG. 7, an alternative embodiment of the present invention including a method for introduction of a temperature probe to a position distal and retrograde from the opening of a sheath is presented. In this embodiment, sheath 205 is inserted into vessel 200 in a manner well-known to those skilled in the art. Once sheath 205 has been inserted into vessel 200, an introducer tube 210 may be inserted into the proximal opening of the sheath 205 and advanced through the lumen of sheath 205. The introducer 210 may be formed from an appropriately biocompatible material that is stiff in some portions of the introducer, but flexible at the distal end of the introducer. In this manner the introducer tube may be formed such that the distal end of the introducer 210 has a flexible "J"shaped construction that allows the introducer 210 to be inserted into advanced through the lumen of sheath 205, the flexible "J" shaped distal end of the introducer conforming to the configuration of the walls of the sheath, until the distal end of introducer 210 is advanced beyond the distal end of sheath 205. As shown in FIG. 8, once the distal end of introducer 210 has advanced beyond the distal opening of sheath 205, the retained flexibility of the "J"shaped introducer 210 causes the distal end of introducer 210 to return to its original shape, springing into a "J" shaped tube.

As shown in FIG. 8, once introducer 210 has returned to its original "J" shape, the distal opening of introducer 210 now points in a direction upstream, or retrograde, of the blood flowing though vessel 200. A temperature sensing probe, for example, in the form of a steerable wire 215 having a temperature sensor 220 mounted on the distal end thereof may then be advanced through the lumen of introducer 210 out through the distal opening of introducer 210. The "J" shape of introducer 210 directs the distal end of wire 215 having temperature sensor 220 mounted thereon in a retrograde direction within vessel 200, allowing temperature sensor 220 to be advanced and navigated to a location retrograde of the sheath 205 relative to the blood flow in vessel 200.

Once temperature sensor 220 has been positioned at the desired location within vessel 200, introducer 210 may be pulled back through the lumen of sheath 205. As introducer 200 is pulled back within sheath 205, the flexible walls of the distal portion of the introducer 210 allow the "J" shaped distal end of introducer 210 to straighten so that introducer 210 may be pulled back within the lumen of sheath 205, leaving temperature sensor 220 positioned within vessel 200 as shown in FIG. 10. Introducer 210 will typically be pulled back through the lumen of sheath 205 until introducer 210 is pulled completely out of sheath 205 since the lumen of sheath 205 will typically be needed to be relatively free of obstruction so that additional catheters, may be advanced through the lumen of the sheath into vessel 200, such as a heat exchange catheter described above. In most cases, although not all, introducer 210 will be completely removed from sheath 205, as shown in FIG. 10, so that sheath 20 will be free from any obstruction that may impeded insertion of catheters or other devices into the vessel through sheath 205.

When the procedure is completed, temperature sensor 220 may be removed from the lumen of vessel 200 by pulling wire 215 backward out of the sheath until the temperature sensor is drawn within the lumen of sheath 205 and then removed from the body. The wire will generally be soft enough to simply withdraw through the introducer. On rare occasions, however, it may be beneficial to protect the vasculature of the patient from any undesirable affects that may be caused by simply pulling wire 215 from the body. In theses cases, introducer 210 may again be advanced over wire 215 through the lumen of sheath 205 until the distal end of introducer 210 returns to its "J" shape, as depicted in FIG. 8. Once introducer 210 has been advanced to this position, wire 215 may be pulled backwards through the lumen of introducer 210 which will guide wire 215 and temperature sensor 220 as they are pulled towards the distal opening of the distal end of introducer 210. In this manner, the "J" shape of introducer 210 allows for improved guidance of wire 215 and temperature sensor 220 as they are pulled from the body at the completion of the procedure.

As described previously, introducer 210 will typically be completely removed from the central lumen of sheath 205 to enable the insertion of other catheters through sheath 205 into the blood vessel 200. In one embodiment, introducer 210 may be formed as a removable sleeve inside the sheath 205 which can be withdrawn and peeled away from the wire 215. In this embodiment, the outer diameter of the introducer 210 may be only slightly less than the inner diameter of the lumen of sheath 205. When introducer 210 is pulled back into the lumen of sheath 205, introducer 210 may be likened to a lining of sheath 205. Since the inner lumen of introducer 210 is only slightly less than the inner lumen of sheath 205, additional catheters, such as a heat exchange catheter, may be advanced through the central lumen of introducer 210 into vessel 200.

In yet another embodiment, introducer 210 may include both a central lumen and a second, smaller, lumen. A stiffening mandrel may be inserted through the second smaller lumen and used to straighten the distal "J" shaped end of introducer tube 210 so that it may be pulled back through the distal opening of the central lumen of sheath 205. In still another embodiment, introducer 210 may be flexible enough so that simply inserting another catheter, such as a heat exchange catheter, which may, although not necessarily, include a stiffening guide wire, may be sufficient to straighten introducer 210. Keeping in mind that the catheter needs to be atraumatic to a patient's vasculature, the introducer 210 must be sufficiently flexible relative to the catheter so that the catheter can straighten the "J" shape without being so stiff as to be traumatic to the vessel.

FIGS. 11 and 12 depict another alternative embodiment of the present invention. In this embodiment, a sheath 250 has a central lumen 255 and smaller side lumen 260. A temperature probe wire 275 may be inserted in the proximal opening of side lumen 260 and advanced therein. Temperature probe wire 275 may be formed from a material having a memory so that the material will tend to return to an initial shape after the probe wire is deformed or its configuration changed, such as when it is inserted into the lumen of a sheath, and then is released from the constraints, such as when it is advanced out of the sheath. The probe wire 275 may, for example, include a bend located at a position proximal to the distal end of wire 275 such that when wire 275 is fully extended, a temperature sensor 280 mounted on the distal end of wire 275 will be positioned in a retrograde position relative to the location of the bend in wire 275. Wire 275, however, is sufficiently flexible so that when the distal end of wire 275 and temperature sensor 280 is inserted into the proximal end of side lumen 260, wire 275 may be threaded through lumen 260 in such a manner that the lumen 260 causes the bend in wire 275 to straighten out sufficiently to allow wire 275 to be advanced through lumen 260. An opening 265 is located along the length of side lumen 260. Additionally, side lumen 260 is blocked by a termination or end wall portion 270. Wall portion 270 is curved in such a manner so that as wire 275 is threaded through lumen 260, the distal end of wire 275 and the temperature sensor 280 are directed through opening 265. To further assist in the retrograde placement, the portion of the wall adjacent opening 262 may be in the form of a ramp 270' that directs the wire retrograde when it is advanced through the opening.

Once the distal end of wire 275, including temperature sensor 280, is directed through opening 265 a sufficient distance, the bend in wire 275 and the flexible memory of wire 275 cause the distal end of wire 275 to curve around so that further advancement of wire 275 in direction A, as shown in FIG. 12, results in the temperature sensor mounted on the distal end of wire 275 moving into the lumen of a vessel in a retrograde fashion. Further advancement of wire 275 will result in the distal end of wire 275 and temperature sensor 280 moving further in the direction opposite to direction A to locate the temperature sensor proximal to opening 265. This structure allows retrograde positioning of the temperature sensor 280 while leaving the sensor lumen 255 of sheath 250 open so that it can be used for the advancement of other catheters, such as a heat exchange catheter as described above. When the procedure is completed and sheath 250 is to be removed from the lumen of the vessel, wire 275 may be pulled back through side lumen 260 in a direction opposite to direction A as shown in FIG. 12. Pulling wire 275 back in a direction opposite to direction A results in the distal end of wire 275 moving towards the distal end of sheath 250, where it is drawn back through opening 265 into side lumen 260.

Alternatively, the embodiments depicted in FIGS. 11 and 12 may be used in conjunction with a temperature probe wire 260 that does not have a bend formed in it prior to insertion through lumen 260. Wire 260 may be formed a material that is soft and flexible enough to be deflected and/or deformed by ramp 271 and wall 270 so that advancement of the wire through lumen results in retrograde position of the temperature sensor or sensors 280.

Further embodiments of the present invention are depicted in FIGS. 13–15. As illustrated in FIGS. 13 and 14, a sheath 300 having a central lumen 302 and a distal end 305 is formed to include a capture tube 310. Capture tube 310 may be formed by including an additional lumen either integrally formed with sheath 300 or formed as a separate lumen and then attached to the distal end of sheath 300. Capture tube 310 has a center lumen 312 of a sufficient diameter to receive a temperature probe wire 315 having a temperature sensor 325 mounted to the distal end thereof. Capture tube 310 also includes a proximal opening 330 and a distal opening 320.

In use, sheath 305 is inserted into the lumen of a blood vessel with temperature wire 315 extending through central lumen 302. Temperature wire 315 is formed such that it includes a bend at a selected location along the length of wire 315 such that the distal end of wire 315 and temperature sensor 325 attached thereto extend in a retrograde fashion along the length of wire 315. The distal end of wire 315, including temperature sensor 325, are inserted through the distal opening 320 of capture tube 310 and extend through the central lumen 312 such that during insertion of the sleeve 305 into a body lumen or vessel the temperature sensor 325 may be disposed within lumen 312 just distal to proximal opening 330 of capture tube 310. In this manner, the temperature sensor may be protected during insertion of the sheath 300 through the skin of the patient and into the vessel.

Once the sheath is in position within the vessel, the wire 315 may be pulled in direction A, as shown in FIG. 14, to move the distal end of wire 315 and temperature sensor 325 in the direction indicated by direction A to position the temperature sensor 325 to a location retrograde relative to the distal end of the introducer sheath. When withdrawal of sheath 305 from the vessel lumen is desired, wire 315 is advanced in a direction opposite to direction A, moving temperature sensor 325 back within proximal opening 330 of capture tube 310. In one embodiment, a stop 321 is disposed on the wire just proximal of the temperature sensor may stop the further movement of the wire once it has been adequately withdrawn to bring the temperature sensor into the capture tube. The opening of the capture tube at 320 may have a smaller diameter than the diameter of the stop, and further movement of the wire will not be possible once the probe has been fully retracted. Since this action will take place in the patient's vessel and out of the sight of the physician, this will also provide a tactile signal that the sensor is properly placed. Once the temperature sensor 325 is completely within lumen 312 of capture tube 310, sheath 300 may be withdrawn from the vessel and through the skin. This embodiment of the present invention allows withdrawal of sheath 305 without snagging the distal end of wire 315 and temperature sensor 325 on the vascular anatomy or other tissue of the patient. The stop 271 may be formed from any suitable biocompatible material and is positioned on the wire 315 as desired to ensure both proper advancement and retraction of the temperature sensor 325. The stop 271 may be either fixed in position, or it may be adjustable to vary the length of the distal end of wire 315 as needed.

An alternative embodiment of the invention illustrated in FIGS. 13 and 14 is shown in FIG. 15. In the embodiment of FIG. 15, wire 315 does not extend through lumen 302 of sheath 305. Rather, wire 315 is mounted entirely external to sheath 300, except for a portion of wire 315 that is inserted through the distal opening 320 of capture tube 310 and extends through lumen 312. As is readily ascertained, temperature sensor 325 is located within lumen 312 of capture tube 310 during insertion and withdrawal of sheath 300 from a patient's body. When sheath 300 is suitably located within the lumen of a blood vessel, wire 315 may be advanced or withdrawn as necessary to locate temperature sensor 325 within the vessel as desired. Although not shown in FIG. 15, a stop may be mounted on wire 315 as described above with reference to FIG. 13, and distal opening 320 may be sized to have a diameter larger than the diameter of wire 315 but smaller than a diameter of the stop, so that the stop interacts with the distal opening 320 to limit the length of wire 315 that may be withdrawn into lumen 312.

Figure 16:
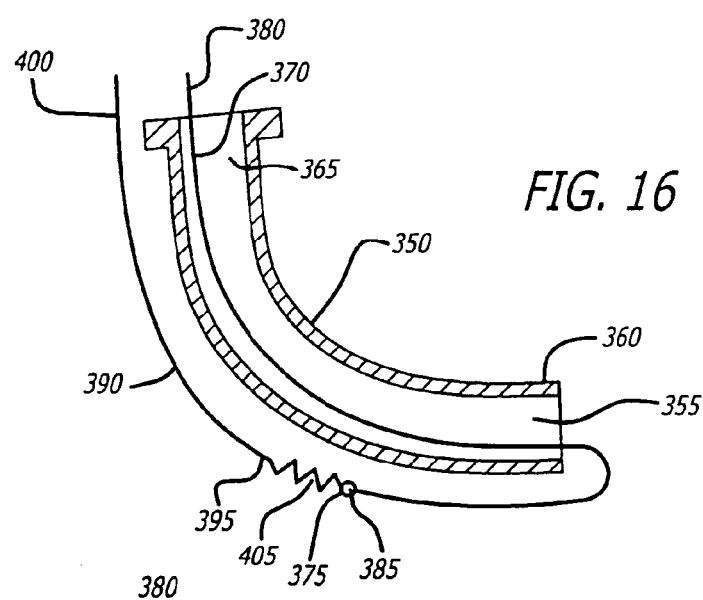
FIG. 16 depicts an alternative embodiment of the present invention showing a temperature probe wire having a detachable portion attached to the wire by a breakaway portion.
Figure 17:
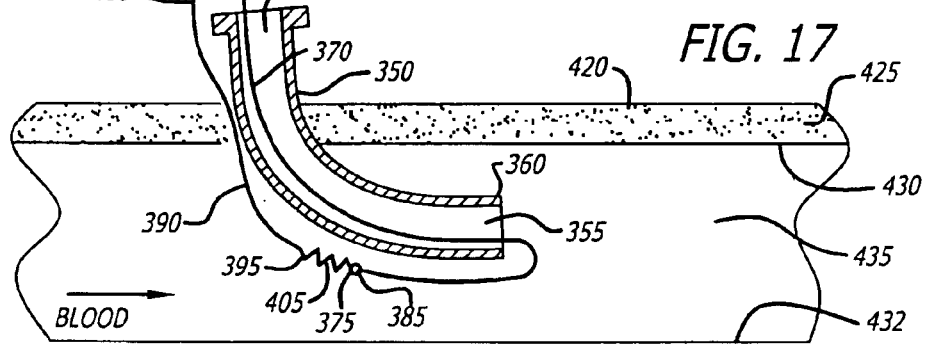
FIG. 17 shows the embodiment of FIG. 16 inserted in the lumen of a blood vessel.
Figure 18:
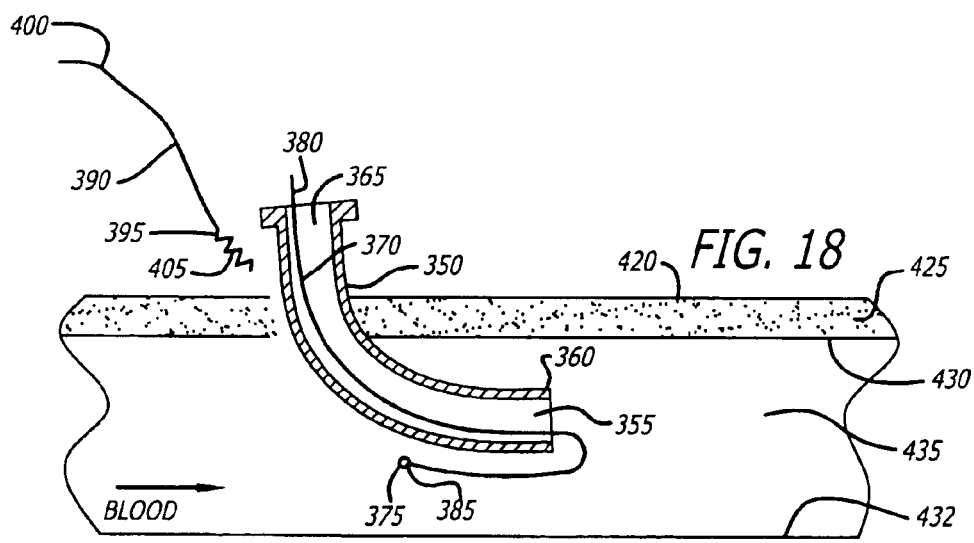
FIG. 18 shows the embodiment of FIGS. 16 and 17 inserted in a lumen of the blood vessel with the detachable portion of the temperature probe wire separated from the temperature probe and removed from the vessel.

FIGS. 16–18 depict still another embodiment of the present invention providing for positioning a temperature sensor within a vessel in a location retrograde relative to the direction of the sheath. In this embodiment, a sheath 350 having a distal opening 360, a proximal opening 365, and a central lumen 355 extending therebetween, may have a temperature wire 370 inserted through the proximal opening 365 and extending through lumen 355 and out distal opening 360. Temperature wire 370 has a proximal end 380 and distal end 385. Temperature wire 370 has a proximal end 380 and a distal end 385. Temperature sensor 375 is mounted at distal end 285. Wire 370 further has a detachable portion 390 which has a first end 395 and a second end 400. Detachable portion 390 of wire 370 is attached to the distal end 385 of wire 370 by way of a break apart section 405.

Break apart section 405 may be attached directly to temperature sensor 385, or it may be otherwise attached to distal end 375 of wire 370. Break apart section 405 may be biodegradable, that is, for example, blood soluble, or it may be formed from any biocompatible material that is sufficiently weak and may be easily pulled apart. For example, holding proximal end 380 of wire 370 in a stationary position and attempting to withdraw second end 400 of detachable portion 390 in an outward direction may to apply sufficient tension across break apart section 405 to cause break apart section 405 to separate from distal end 375 of wire 370.

FIGS. 17 and 18 illustrate the embodiment depicted in FIG. 16 disposed within a blood vessel. As shown in FIG. 17, sheath 350 is inserted through skin 420 through various epidermal and muscle layers 425 and through vessel wall 430 into lumen 435 of blood vessel 432. When sheath 350 is inserted through skin 420 into lumen 435, wire 380 is positioned such that temperature probe 385 is protected within the lumen 355 of sheath 350. Once sheath 350 is satisfactorily inserted within lumen 435, wire 370 may be advanced through lumen 355 of sheath 350 while the end 400 of disposable portion 390 is withdrawn from the wound. This advancement and withdrawal of wire 370 and detachable portion 390 results in moving distal end 375 of wire 370 through the distal opening of sheath 350 around the edge of sheath 350 and pulls the temperature sensor 385 along the outer wall of sheath 350 to a desired location retrograde of the distal opening of sheath 350.

Once temperature sensor 385 is positioned in the desired location retrograde of the distal end 360 of sheath 350, force may be applied to end 400 of detachable portion 390 to cause breakaway portion 405 to pull away from distal end 375 of wire 370, thus separating detachable portion 390 from wire 370. When breakaway portion 405 separates, detachable portion 390 may be pulled until the entire length of detachable portion 390 is withdrawn from the patient's body, leaving temperature sensor 385 in the desired location within lumen 435 of vessel 432. In this embodiment, wire 370 may be sized such that there is sufficient space within lumen 355 of sheath 350 to allow advancement and retraction of other catheters, such as a heat exchange catheter as described above, though lumen 355. When the procedure is completed and sheath 350 is about to be withdrawn from lumen 435 of vessel 432, force maybe applied to end 380 of wire 370 to withdraw wire 370 from sheath 350, causing distal end 375 to enter distal opening 360 of central lumen 355 of the sheath and then be withdrawn from the patient's vessel.

Figure 19:
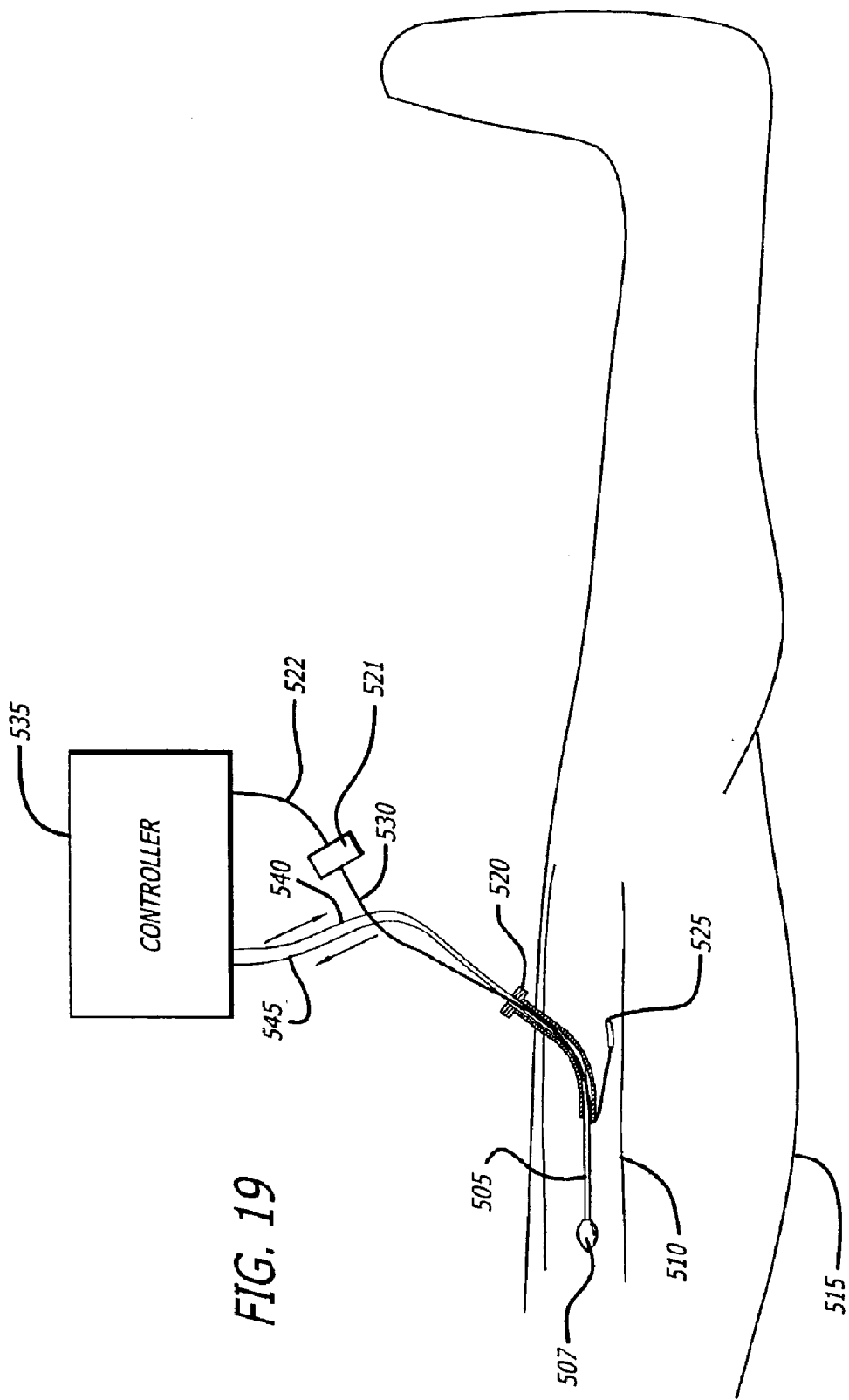
FIG. 19 is a schematic view showing a temperature probe positioned retrograde of the opening of an introducer sheath in a blood vessel of a patient, the temperature probe connected to a controller and controlling the delivery of heating or cooling fluid into a patient.

FIG. 19 depicts a heat exchange system utilizing a heat exchange catheter 505 having a heat exchange region, here depicted as a balloon 507, inserted in a femoral vein 510 of a patient's leg 515. The heat exchange catheter 505 is inserted through sheath 520 into vein 510. Temperature probe 525, in accordance with aspects of the present invention described above, is also inserted through sheath 520 in such a manner as to position temperature sensor or sensors 520 at a location retrograde of the distal opening of sheath 520 and heat exchange balloon 507. A conductor 530 electrically connects temperature sensor or sensors 525 with controller 535. Conductor 530 conducts electrical signals generated by temperature sensor or sensors 525 to controller 535, in response to which controller 535 controls the temperature or rate of flow, or both, of heat exchange fluid circulating through balloon 507 through fluid input conduit 540 and fluid return conduit 545.

Figure 20:
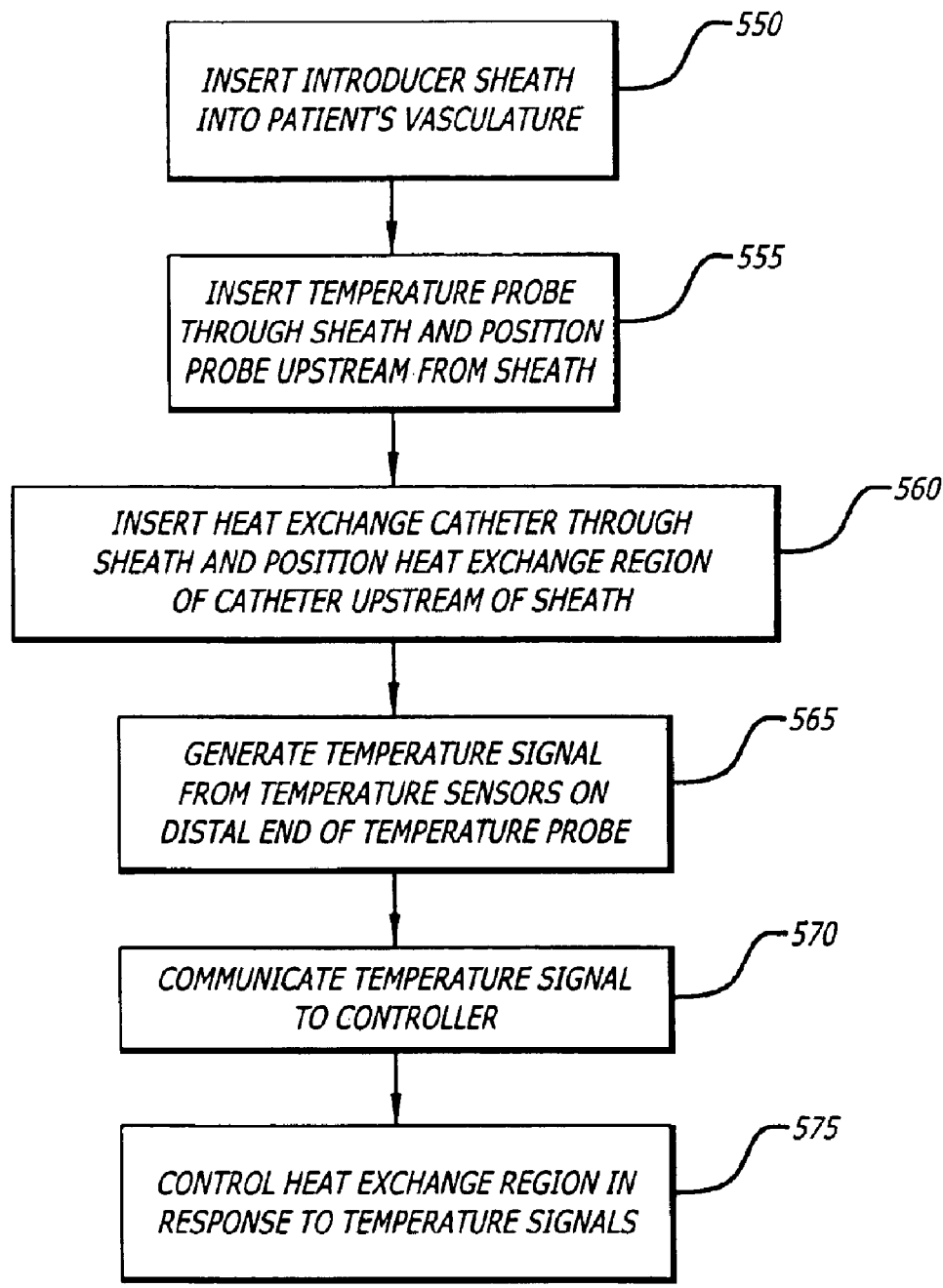
FIG. 20 is a block diagram of a method for positioning a temperature probe in a position retrograde of an opening in an introducer sheath to generate temperature signals that transmitted to a controller which then controls the delivery of heating or cooling fluid to a heat exchange device located in a patient's blood vessel at a position antegrade of the temperature probe in accordance with the generated signals.

FIG. 20 is a block diagram depicting a method for positioning a heat exchange catheter and a temperature probe into the vasculature of a patient to alter or maintain the temperature of a target tissue or the body core of the patient. In box 550, an introducer sheath is inserted through the tissue of a patient's body and into the lumen of a selected portion of the vasculature of the patient. A temperature probe having temperature sensors disposed on a distal end of the temperature probe is inserted through the introducer sheath and positioned in the lumen of the patient's vasculature at a location retrograde of the distal opening of the introducer sheath in box 555.

In box 560, a heat exchange catheter having a heat exchange region is inserted through the introducer sheath and advanced through the patient's vasculature until the heat exchange region is in a desired position within the vasculature downstream of the distal opening of the introducer sheath. The input and return fluid lines of the heat exchange catheter are connected to a heat exchanger and pump that is controlled by a controller, which may be, but not necessarily, microprocessor based. Conductors of the temperature probe in electrical communication with the sensor or sensors of the probe are also placed in electrical communication with controller. This connection may be a hard wired connection, or alternatively, the temperature sensors may communicate with the controller using wireless means, such as radio frequency, infra red, blue tooth, or other scheme capable of communicating signals representing the temperature of the fluid sensed by the temperature sensors from the sensors to the controller.

Signals generated by the temperature sensors (box 565) are communicated to the controller in box 570. In box 575, the controller, in response to the signals communicated from the sensor or sensors, adjusts the rate of flow of heat exchange fluid or temperature of the fluid, or both, that is circulated to the heat exchange balloon. In this manner, the amount of heating or cooling of the blood that flows past the heat exchange balloon may be controlled so as to accurately and efficiently control the heating or cooling of the target tissue or body core of the patient.

FIGS. 21A through 21C and 22A through 22C depict yet another embodiment of the present invention. This embodiment provides a system wherein a temperature probe may be deployed into a retrograde position relative to an introducer sheath, and then retracted and removed from the patient's vessel. This embodiment includes a deployment catheter 600 that may be inserted through the proximal opening (not shown) of an introducer 602, advanced through lumen 605 of introducer 602 until distal end region 610 of the deployment catheter 600 extends out of and beyond distal opening 607 of introducer 602. At least distal region 610 of deployment catheter 600 is formed from a compressible material that has a memory such that the distal region has a compressed diameter that is smaller than the diameter of the lumen 605 of introducer 602, and an expanded diameter that is larger than the diameter of the lumen 605 of introducer 602. In one embodiment, a slot 615 may be formed in one or more areas of distal end region 610 so as to assist in compressing distal end region 610 to the compressed diameter. As depicted in FIGS. 21A through 22C, slot 615 is formed having an open side disposed at a the distal end 612 of distal end region 610, separating distal end 612 into two or more segments, depending on the number of slots formed therein. These segments, because they are spaced apart from one another by the open end of the slot 615, can move towards one another to provide the compressed diameter of distal end region 610. Alternatively, distal end region may be formed from a flexible material that allows the wall of distal end region 610 to fold into a compressed diameter when the distal end region 610 is disposed within lumen 605, and unfold and expand to an expanded diameter when distal end region 610 is advanced beyond distal opening 607 of introducer 602.

As shown in FIG. 21A, distal end region 610 of deployment catheter 600 is advanced through lumen 605 of introducer 602. Distal end region 610 also includes a guide tube 620 disposed on an inner surface of the wall of distal end region 610. Guide tube 620 includes a lumen extending between a proximal opening 622 and a distal opening 623. A probe 625 having a bend region 630 and a distal region 632 is disposed with a lumen of the deployment catheter 600 such that the distal region 632 of probe 625 extends through the lumen of the guide tube 620 out of distal opening 622 of guide tube 620. A temperature sensor 635 is disposed at the tip of distal region 632 of probe 625.

When distal end region 610 is advanced sufficiently beyond distal opening 607 of introducer 602, as depicted in FIG. 21B, distal end region 610 expands to its expanded diameter. When distal end region 610 expands to its expanded diameter, a port 640 formed in at least a portion of the proximal end of the distal end region 610 opens to form a pathway between the interior lumen of distal end region 610 and the area exterior to the introducer 602. Thus, when the system as described is used to locate a temperature probe within a vessel retrograde to the distal opening of the introducer, port 640 provides a pathway between the interior of the deployment catheter 600 and the blood stream. Once port 640 is open, probe 625 may be pulled in a proximal direction, pulling the distal region 632 of the probe 625, and thus temperature sensor 635, through port 640 in a retrograde direction to position temperature sensor 635 at a location retrograde of the distal end of the introducer 602, as is shown in FIG. 21C. In this embodiment, bend region 630 of probe 625 interacts with the distal end of the guide tube 620 to limit the extent that temperature sensor 635 may be moved in a retrograde direction. Accordingly, the length of distal region 632 of probe 625 by be sized to provide a controlled positioning of temperature 635 in a retrograde location relative to the distal end of the introducer.

It will be understood that deployment catheter 600 has a central lumen through which the probe is advanced and removed. The central lumen of deployment catheter 600 has a diameter large enough to allow the advancement and removal of other catheters, such as a heat exchange catheter, through the lumen while the temperature sensor is deployed in a retrograde location. Moreover, port 640 in distal end region 610 also provides a pathway for blood or other bodily fluid to flow through the distal end region of the deployment catheter 600 when the distal end region 610 is in its expanded state. This allows the expanded diameter of distal end region 610 to be as large as the inner diameter of a vessel lumen without obstructing the flow of blood or other body fluid through the vessel.

FIGS. 22A through 22C depict the removal of the temperature probe and deployment catheter of FIGS. 21A through 21B from a patient's vessel. As shown in FIG. 22b, probe 625 is advanced in a distal direction, causing temperature sensor 635 disposed on the tip of distal region 632 to be pulled back into the interior of distal end region 610 of deployment catheter 600.

Once temperature sensor 635 is positioned within the interior of distal end region 610, deployment catheter 600 may be pulled toward the proximal end of introducer 602, collapsing distal end region 610 into its compressed state, as shown in FIG. 22C. In this manner, a temperature sensor may be deployed in a retrograde location in a patient's vessel, and then removed from the vessel such that the sensor is protected during deployment and removal, and the vascular tissue is also protected from abrasion or laceration caused that could occur if the probe were not protected by the deployment catheter when the temperature sensor is deployed or removed.

While the invention has been described in connection with certain disclosed embodiments, it is not intended to limit the scope of the invention to the particular forms set forth, but, on the contrary it is intended to cover all such alternatives, modifications, combinations and equivalents as may be included in the spirit and scope of the invention as defined by the appended claims.

What is claimed:

1. A temperature sensing system for determining the core body temperature of a patient by measuring the temperature of body fluid flowing within a body lumen, comprising: a sheath having a proximal end having a proximal opening, a distal end region having a distal opening disposed at a distal tip of the distal end region, and a lumen therebetween; a wire probe configured to be inserted into the proximal opening of the sheath into the lumen of the sheath, the wire probe having a proximal end region, at least a portion of which may be used to advance and retract the wire probe through the sheath, and a distal end region having a distal tip, the distal end region being defined by the distal tip and an acute bend located proximal to the distal tip such that the distal end region is shorter than the proximal end region, the acute bend being the leading portion of the wire probe as it is advanced through the lumen of the sheath, the distal end region having a first uncompressed position before the distal region is inserted in the lumen of the sheath and a second, compressed position when the distal region is inserted into the lumen of the sheath; at least one temperature sensor disposed at the distal tip of the wire probe; whereby the distal end region of the wire probe returns to its first position when the distal tip of the distal end region is advanced beyond the distal opening of the sheath, and wherein the distal tip and temperature sensor may be moved to a position proximal of the distal end opening of the sheath by withdrawing at least a portion of the proximal end region of the wire probe from the sheath.

2. The system of claim 1, wherein the sheath has a first portion having an inserted length; and wherein the distal end region of the wire probe has a length that is longer than the inserted length of the sheath.

3. The system of claim 1, wherein the at least one temperature sensor is a thermistor.

4. The system of claim 1, wherein the least one temperature sensor is a thermocouple.

5. The system of claim 1, wherein the at least one temperature sensor is housed in a thermally conductive, electrically insulative material.

6. The system of claim 1 further comprising a controller unit configured to receive temperature signals representative of a temperature of the body fluid from the at least one temperature sensor, and also for providing indications representative of the temperature, and a coupler for coupling the at least one temperature sensor to the controller unit.

7. The system of claim 1, further comprising a heat exchange catheter having a heat exchange region.

8. The system of claim 6, further comprising a heat exchange catheter having a heat exchange region.

9. The system of claim 8, wherein the heat exchange region has a temperature that is controlled by the controller in response to the temperature signals.

* * * * *

UNITED STATES PATENT AND TRADEMARK OFFICE
CERTIFICATE OF CORRECTION

PATENT NO. : 6,866,638 B2
DATED : March 15, 2005
INVENTOR(S) : Michael W. Dae et al.

It is certified that error appears in the above-identified patent and that said Letters Patent is hereby corrected as shown below:

Drawings,
Sheet 2 of 13, delete Fig. 2A.

Column 3,
Line 31, delete "uring" and insert -- urine --.

Column 5,
Line 60, delete "and" and insert -- an --.

Column 6,
Line 19, delete "includes" and insert -- include --.

Column 7,
Line 1, delete "and other" and insert -- another --.

Column 8,
Line 46, after "provides" insert -- an --.

Column 9,
Line 32, delete "maybe" and insert -- may be --.

Column 13,
Line 54, after "inserted into" insert -- and --.

Column 14,
Line 39, delete "theses" and insert -- these --.

Column 16,
Line 2, after "may be formed" insert -- of --.
Line 43, after "a stop 321" delete "is".

Column 18,
Line 7, delete "though" and insert -- through --.

UNITED STATES PATENT AND TRADEMARK OFFICE
CERTIFICATE OF CORRECTION

PATENT NO. : 6,866,638 B2
DATED : March 15, 2005
INVENTOR(S) : Michael W. Dae et al.

It is certified that error appears in the above-identified patent and that said Letters Patent is hereby corrected as shown below:

Column 20,
Line 3, delete "by" and insert -- may --.
Line 36, delete "caused".

Signed and Sealed this

Sixteenth Day of August, 2005

JON W. DUDAS
*Director of the United States Patent and Trademark Office*